US00RE38963E

(19) United States
(12) Reissued Patent
Cuberes-Altisent et al.

(10) Patent Number: US RE38,963 E
(45) Date of Reissued Patent: Jan. 31, 2006

(54) PYRAZOLINE DERIVATIVES, THEIR PREPARATION AND APPLICATION AS MEDICAMENTS

(75) Inventors: Maria Rosa Cuberes-Altisent, Barcelona (ES); Juana Maria Berrocal-Romero, Barcelona (ES); Maria Montserrat-Contijoch-Llobet, Barcelona (ES); Jordi Frigola-Constansa, Barcelona (ES)

(73) Assignee: Laboratorios del Dr. Esteve, Barcelona (ES)

(21) Appl. No.: 10/229,880

(22) PCT Filed: May 27, 1999

(86) PCT No.: PCT/ES99/00156

§ 371 (c)(1),
(2), (4) Date: Nov. 28, 2000

(87) PCT Pub. No.: WO99/62884

PCT Pub. Date: Dec. 9, 1999

Related U.S. Patent Documents

Reissue of:
(64) Patent No.: 6,353,117
Issued: Mar. 5, 2002
Appl. No.: 09/701,276
Filed: Nov. 28, 2000

(30) Foreign Application Priority Data

May 29, 1998 (ES) ..... 9801129

(51) Int. Cl.
*C07D 231/06* (2006.01)
*A61K 31/41* (2006.01)

(52) U.S. Cl. ..... 548/379.4; 548/379.7; 514/403

(58) Field of Classification Search ..... 548/379.4, 548/379.7; 514/404
See application file for complete search history.

(56) References Cited

U.S. PATENT DOCUMENTS 4,425,179 A * 1/1984 Bauer et al. ..... 156/397.5

FOREIGN PATENT DOCUMENTS

WO 8806583 9/1988

OTHER PUBLICATIONS

Dhar, et al *Reaction of Chlorosulphonyl Isocyanate with 2–Pyrazolines*, Indian Journal of Chemistry, vol. 23B, Dec. 1984, pp. 1187–1189.
Mokhtar, H. *Synthesis of Nitrogenous Compounds from 4–Unsatur 1,3–Dicarbonyl Esters*, Part 1, J. Chem. Soc. Pak, vol. 10, No. 4, 1988.
P. Catsolulacos, *Synthesis of Substituted Pyrazolines*, Chron. (1966) 31(1) pp 1–2.
J. Hernandez, *The negative inotropic effect of diazepram in rat right ventricular strips*, J. Pharm. Pharmacol. 1991 vol. 43 pp. 879–881.
Mokhtar, H *Synthesis of Nitrogenous Compounds*, Part 2, Pak, J. Sci. Ind. Res, vol. 33, Nos. 1–2, Jan., Feb., 1990.
Feid–Allah, H. *Trisubstituted Pyrazoles of Possible Antidiabetic and Antibacterial Activity*, Pharmazie 36, H. 11 (1981).
Begley, W. et al, Pyrazolo[1,5–f]phenanthridine and Derivatives: Electrochemical and Photochemical Synthesis.

* cited by examiner

*Primary Examiner*—Joseph K. McKane
*Assistant Examiner*—Kamal Saeed
(74) *Attorney, Agent, or Firm*—Ladas & Parry

(57) ABSTRACT

The present invention relates to new pyazoline derivatives of formula (I)

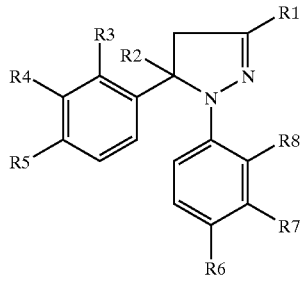

and to physiologically acceptable salts thereof, to the method for their preparation and to their application as medicaments.

23 Claims, No Drawings

PYRAZOLINE DERIVATIVES, THEIR PREPARATION AND APPLICATION AS MEDICAMENTS

Matter enclosed in heavy brackets [ ] appears in the original patent but forms no part of this reissue specification; matter printed in italics indicates the additions made by reissue.

This application is a 371 of PCT/ES99/00156 filed on May 27, 1999.

FIELD OF THE INVENTION

The present invention relates to new pyrazoline derivatives, of general formula (I), and to physiologically acceptable salts thereof, to the procedures for their preparation, to their application as medicaments in human and or veterinary therapy and to the pharmaceutical composition that contain them.

(I)

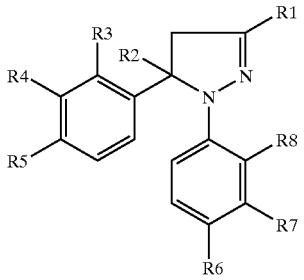

The new compounds object of the present invention can be used in the pharmaceutical industry as intermediates and for the preparation of medicaments.

BACKGROUND OF THE INVENTION

Non-steroid anti-inflammatory drugs (NSAIDS) are traditionally classified as anti-inflammatory, antipyretic and analgesic agents for the symptomatic alleviation of inflammation, fever and light to moderate pain. The main indications for these drugs are osteoarthritis, rheumatoid arthritis and other inflammatory diseases of articulations, as well as for the treatment of inflammations associated with small lesions and as analgesics of broad use. The NSAIDS are essentially inhibitors of acute inflammatory response, but in rheumatic disorders they have little effect on the underlying degenerative changes occurring in tissue.

The discovery of the main mechanism of action of the NSAIDS by inhibition of cyclooxygenase (COS) [J R. Vane, Nature, 1971, 231, 232] provided a satisfactory explanation of their therapeutic action and established the importance that certain prostaglandins have as mediators in inflammatory disease [R. J. Flower, J. R. Vane, Biochem. Pharm., 1974, 23, 1439; J. R. Vane, R. M. Botting, Postgrad Med. J., 1990 66(Suppl 4), S2]. The gastric toxicity of the classic NSAIDS, as well as their beneficial effects, is due to the suppression of prostaglandin synthesis by inhibition of the COX enzyme. Although several strategies have been followed (enteral Coating to prevent adsorption in the stomach, parenteral administration, pro-drug formulation, etc) to reduce the gastrointestinal lesions provoked by the NSAIDS, none of these modifications have provided a significant impact on the incidence of serious adverse reactions such as perforation and haemorrhaging.

The discovery of an induced prostaglandin-synthetase, denominated cyclooxygenase-2 (COX-2), different from the constitutive enzyme, currently denominated cyclooxygenase-1 (COX-1) [J. Sirois, J. R. Richards, J. Biol. Chem., 1992, 267, 6382], has renewed the interest in the development of new anti-inflammatory drugs. The identification of the isoform COX-2 has led to the hypothesis that it could be responsible for the production of prostaglandins in places where inflammation occurs. As a result, selective inhibition of this isoenzyme would reduce the inflammation without producing the side effects of gastric and renal toxicity. The COX-1 isoenzyme is essentially expressed in most of tissues with the function of synthesising prostaglandins which regulate the normal cell activity. On the other hand, the isoenzyme COX-2 is not normally present in cells but in chronic inflammation the levels of the protein COX-2 increase in parallel with the over-production of prostaglandins [J. R. Vane, R. M. Hotting, Infalmm. Res., 1995, 44, 1]. Therefore, a selective COX-2 inhibitor has the same anti-inflammatory, antipyretic and analgesic properties as a conventional non-steroid anti-inflammatory agent and also inhibits the uterine contractions induced by hormones and presents potential anti-carcinogenic effects and beneficial effects in the prevention of the development of Alzheimer disease. On the other hand, a selective COX-2 inhibitor reduces the potential gastrointestinal toxicity, reduces the potential renal side effects and reduces the effects of bleeding time.

The tri-dimensional structure of COX-1 has been determined by x-ray diffraction [D. Picot, P J. Loll, R. M Garavito, Nature, 1994, 367, 243]. Three of the helixes of the structure form the entrance to the cyclooxygenase channel and its insertion in the membrane allows the arachidonic acid to access the active site from inside the bilayer. The active site of cyclooxygenase is a large hydrophobic channel and the authors argue that the NSAIDS inhibit COX-1 by excluding arachidonic acid from the upper part of the channel. Recently [R. S. Service, Science, 1996, 273, 1660], the three-dimensional structure of COX-2 has been described, which allows comparison of the similarities and differences between the two isoforms and therefore study of new drugs that selectively inhibit COX-2. The structures of COX-1 and COX-2 show that the sites where the anti-inflammatory agents bind to the enzymes are very similar but there is a difference of at least one important amino acid. A voluminous isoleucine present in the active site of COX-1 is replaced by a valine in COX-2. The isoleucine blocks the lateral cavity that is separated from the principle bond of both isoenzymes. The blocked cavity of COX-1 does not impede the binding of classic NSAIDS, but an inhibitor that needs the extra support point supplied by the lateral cavity will bind more easily to COX-2 than to COX-1. As a result, a model for a new generation of anit-inflammatory agents is one where the inhibitors of cyclooxygenase have a large preference for the lateral cavity of COX-2.

In the chemical literature derivatives of nitrogenated heterocyclic aromatics of five members have been described with COX-2 inhibitory activity. Within these azole derivatives are the pyrrols [W. W. Wilkerson, et al, J. Med. Chem., 1994, 37, 988; W. W. Wilkerson, et al, J. Med. Chem., 1995, 38, 3895; I. K. Khanna, et al, J. Med. Chem., 1997, 40, 1619], pyrazoles [T. D. Penning, et al, J. Med. Chem., 1997, 40, 1347; K. Tsuji, et al, Chem. Pharm. Bull., 1997, 45, 987; K. Tsuji, et al, Chem. Pharm. Bull., 1997, 45, 1475], or imidazoles [Khanna, et al, J. Med. Chem., 1997, 40, 1634].

We have now discovered that the novel compounds derived from pyrazolines of general formula (I) show interesting biological properties and these make them particularly useful for their employment in human and/or veterinary therapy. The compounds object of this invention are useful as agents with anti-inflammatory activity and for other diseases in which cyclooxygenase-2 plays a part, without having the gastric and renal toxicity of the classic NSAIDS.

DETAILED DESCRIPTION OF THE INVENTION

The present invention provides new pyrazolines that inhibit the enzyme cyclooxygenase-2, with application in human and/or veterinary medicine as anti-inflammatories and for other diseases in which cyclooxygenase-2 plays a part, and that have low or no gastric and renal toxicity. These anti-inflammatories therefore have a better safety profile. The new compounds object of the present invention are derivatives of $\Delta^2$-pyrazolines, also known as 4,5-dihydro-1H-pyrazoles. They are therefore nitrogenated heterocyclic compounds. As a result the pyrazoline rings are not planar as opposed to the azoles described previously. The compounds object of the present invention have the general formula (I)

(I)

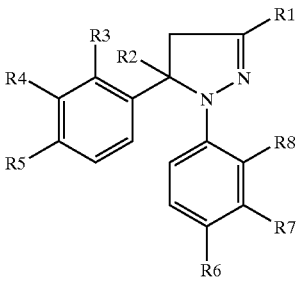

where $R_1$ represents a hydrogen atom, a methyl, fluoromethyl, difluormethyl, trifluoromethyl, carboxylic acid, lower carboxylate of 1 to 4 carbon atoms, carboxamide or cyano group, $R_2$ represents a hydrogen or methyl group, $R_3$, $R_4$, $R_7$ and $R_8$, identical or different, represent an atom of hydrogen, chlorine, fluorine, a methyl, trifluoromethyl or methoxy group, $R_5$ represents an atom of hydrogen, chlorine, fluorine, a methyl, trifluoromethyl or methoxy group, provided that—in all cases—$R_6$ represents a methylsulphonyl, aminosulphonyl or acetoaminosulphonyl group, $R_6$ represents an atom of hydrogen, chlorine, fluroine, a methyl, trifluromethyl or methoxy group, provided that—in all cases—$R_5$ represents a methylsulphonyl, aminosulphonyl or acetoaminosulphonyl group.

For the case that $R_1$ represents a methyl group $R_2$ represents a hydrogen atom or a methyl group, $R_3$ y $R_8$, identical or different, represent an atom of hydrogen, chlorine, fluorine, a methyl or trifluoromethyl group, $R_4$ represents a hydrogen, fluorine atom, a methyl, trifluoro-methyl or methoxy group, $R_5$ represents a fluorine atom, a triflouromethyl or trifluoromethoxy group, provided—in all cases—that $R_6$ represents a methylsulphonyl or aminosulphonyl, $R_6$ represents a hydrogen, chlorine, fluorine atom, a methyl, trifluoromethyl, methoxy or trifluoromethoxy group, provided—in all cases—that $R_5$ represents a methylsulphonyl or aminosulphonyl, and $R_7$ represents a hydrogen, chlorine, fluorine atom, a methyl, trifluoromethyl or methoxy group.

The new compounds of general formula (I) have an asymmetric carbon atom and so can be prepared enantiomerically pure or as racemates. The racemates of compounds (I) can be resolved into their optical isomers by conventional methods, such as separation by chiral stationary phase chromatography for example, or by fractionated crystallisation of its diastereoisomeric salts, which can be prepared by reacting the compounds (I) with enantiomerically pure acids. Similarly, they can also be obtained by enantioselective synthesis using enantiomerically pure chiral precursors.

The present invention also relates to the physiologically acceptable salts of the compounds of general formula (I), in particular, to the addition salts formed with mineral acids such as hydrochloric, hydrobromic, phosphoric, sulphuric, nitric acid, etc, and with organic acids such as citric, maleic, fumaric acid, tartaric acids or its derivatives, p-toluenesulphonic, methanosulphonic, camphosulphonic acid etc.

The novel derivatives of general formula (I) can be used in mammals, including man, as anti-inflammatory agents for the treatment of inflammation and for the treatment of other disorders associated with inflammation, such as analgesics for the treatment of pain and migraine, and as anti-pyretics in the treatment of fever. For example, the new derivatives of general formula (I) can be used in the treatment of arthritis, including but limited to the treatment of rheumatoid arthritis, spondyloarthropathies, gouty arthritis, systemic lupus erythematosus, osteoarthritis and juvenile arthritis. The novel derivatives of general formula (I) can be used in the treatment of asthma, bronchitis, menstrual disorders, tendinitis, bursitis and different states that affect the skin such as psoriasis, eczema, burns and dermatitis. The novel derivatives of general formula (I) can also be used in the treatment of gastrointestinal afflictions such as syndrome of inflamed intestine. Crohn's disease, gastritis, irritated colon syndrome and ulcerous colitis.

The novel derivatives of general formula (I) can be prepared, in accordance with the invention, following the methods that are indicated below:

Method A

The preparation of the compounds of general formula (I) is carried out by reacting a compound of general formula (II)

(II)

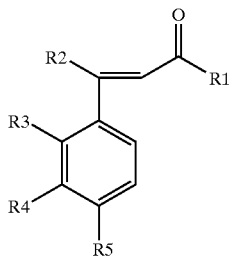

wherein $R_1$ represents a hydrogen atom, a methyl, fluoromethyl, difluoromethyl, trifluoromethyl and carboxylic acid groups, and $R_2$, $R_3$, $R_4$ and $R_5$ have the same meaning as that indicated for general formula (I), with a phenylhydrazine of general formula (III) in base or salt form (III)

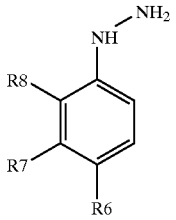

wherein $R_6$, $R_7$ and $R_8$ have the same meaning as that described previously for general formula I.

The reaction is carried out in the presence of a suitable solvent such as, for example, alcohols such as methanol, ethanol, ethers such as dioxane, tetrahydrofuran, or mixtures thereof or other solvents. The reaction takes place in acid medium, that can be organic, such as acetic acid, for example, or inorganic such as hydrochloric acid for example, or a mixture of the two, or in a base medium such as piperidine, piperazine, sodium hydroxide, potassium hydroxide, sodium methoxide or sodium ethoxide for example, or a mixture thereof. The acidic or base medium itself can act as a solvent. The most suitable temperatures vary between room temperature and the reflux temperature of the solvent and the reaction times can lie between several hours and several days.

Method B

The preparation of the compounds of general formula (I), wherein $R_1$ represents an alkyl carboxylate with less than 1 to 4 carbon atoms and $R_2$, $R_3$, $R_4$, $R_5$, $R_6$, $R_7$ and $R_8$ have the same meaning as that given above, is effected by reacting a compound of general formula (I) wherein $R_1$ represents a carboxylic acid group (COOH) and $R_2$, $R_3$, $R_4$, $R_5$, $R_6$, $R_7$ y $R_8$ have the same meaning as that given above, with a suitable reagent to form the acid chloride such as thionyl chloride or oxalyl chloride for example, and then carrying out an esterification reaction with an aliphatic alcohol of 1 to 4 carbon atoms in the presence of an organic base, such as triethylamine or pyridine, or by direct reaction of carboxylic acid with the corresponding saturated anhydrous alcohol with gaseous hydrogen chloride. The reaction is carried out in the reagent as its own solvent or in other appropriate solvents such as halogenated hydrocarbons such as dichloromethane, chloroform or carbon tetrachloride, ethers such as dioxane, tetrahydrofuran, ethyl ether or dimethoxyethane. The most appropriate temperatures vary between 0° C. and the reflux temperature of the solvent and the reaction times lie between ten minutes and 24 hours.

Method C

The preparation of the compounds of general formula (I), wherein $R_1$ represents a carboxamide group and $R_2$, $R_3$, $R_4$, $R_5$, $R_6$, $R_7$ and $R_8$ have the same meaning as that indicated above, is carried out be reacting a compound of general formula (I) in which $R_1$ represents a carboxylic acid group (COOH) and $R_2$, $R_3$, $R_4$, $R_5$, $R_6$, $R_7$ and $R_8$ have the same meaning as that indicated above, with a suitable reagent for forming the corresponding acid chloride, for example, thionyl chloride or oxalyl chloride and then reacting with ammonia, that can be in the form of concentrated aqueous solution or dissolved in a suitable solvent. The reaction is carried out in a suitable solvent such as, for example, ethers such as dioxane, tetrahydrofuran, ethyl ether or dimethoxyethane. The most suitable temperatures vary between 0° C. and the reflux temperature of the solvent and the reaction times lie between 1 and 24 hours.

Method D

The preparation of the compounds of general formula (I), wherein $R_1$ represents a cyano group and $R_2$, $R_3$, $R_4$, $R_5$, $R_6$, $R_7$ y $R_8$ have the same meaning as that indicated above, is carried out by reacting a compound of general formula (I) wherein $R_1$ represents a carboxamide group and $R_2$, $R_3$, $R_4$, $R_5$, $R_6$, $R_7$ and $R_8$ have the same meaning as that indicated above, with a suitable reagent such as, for example, the thionyl dimethylformamide-chloride or methanosulphonyl chloride. The reaction is carried out in a suitable solvent such as, for example, dimethylformamide or pyridine. The most suitable temperatures vary between 0° C. and the reflux temperature of the solvent and the reaction times lies between fifteen minutes and 24 hours.

Method E

The compounds of general formula (II), intermediates in the preparation of the compounds of general formula (I), are commercially available or can be obtained using different known methods among which the following are found:

Method E-1

The preparation of the compound of general formula (II), wherein $R_1$ represents a mono- di- or trifluoromethyl group, $R_2$ represents a hydrogen atom and $R_3$, $R_4$ and $R_5$ have the same meaning indicated above for the compounds of general formula (I), is carried out by reaction of a benzaldehyde of general formula (IV)

(IV)

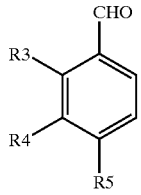

wherein $R_3$, $R_4$ and $R_5$ have the same meaning as that given above for the general formula (I), with N-phenyl(mono, di or trifluoro)acetimidoyl chloride in the presence of a dialkyl phosphonate, such as phosphonate or diethylmethyl, and a strong organic base, such as LDA (lithium diisopropylamide), or by the Wittig reaction with mono-, di- or trifluoroacetylmethylenetriphenylphosphorane and a base such as sodium carbonate or potassium carbonate. The reaction is carried out in a suitable solvent such as, for example, dichloromethane, chloroform or benzene, or an ether such as tetrahydrofurane, ethyl ether, dimethoxyethane or dioxane. The most suitable temperatures vary between −70° C. and the reflux temperature of the solvent, and the reaction times lie between fifteen minutes and twenty hours.

Method E-2

The preparation of the compounds of general formula (II), in which $R_1$ represents a methyl or trifluoromethyl group, $R_2$ represents a methyl group and $R_3$, $R_4$ and $R_5$ have the same meaning indicated above for the compounds of general formula (I), is carried out be reacting a compound of general formula (V)

(V)

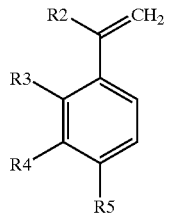

wherein $R_2$ represents a methyl group and $R_3$, $R_4$ and $R_5$ have the same meaning as that indicated above for the compounds of general formula (I), with mono-, di- or trifluoroacetic anhydride in the presence of the complex dimethyl sulphide-boron trifluoride. The reaction is carried out in a suitable solvent such as, for example, halogenated hydrocarbons such as dichloromethane, chloroform or carbon tetrachloride or ethers such as dioxane, tetrahydrofuran, ethyl ether or dimethoxyethane. The most suitable temperatures vary between −70° C. and the reflux temperature of the solvent, and the reaction times lie between twenty minutes an twenty hours.

Method E-3

The preparation of compounds of general formula (II), in which $R_1$ represents a methyl or trifluoromethyl group, $R_2$ represents a hydrogen atom and $R_3$, $R_4$ and $R_5$ have the same meaning as that indicated previously for the compounds of general formula (I), are carried out by different procedures among which can be found, for example, the Claisen-Schmidt reaction between benzaldehyde of general formula (IV) and acetone or 1,1,1-trifluoroacetone in presence of an aqueous solution of alkaline metal hydroxide such as sodium hydroxide or potassium hydroxide or acetic acid and piperidine; the Wittig-Horner reaction between a benzaldehyde of general formula (IV) and a 2-oxo-alkyl phosphonate in the presence of an aqueous solution of a base such as, for example, potassium carbonate or potassium bicarbonate; the reaction of a benzaldehyde of general formula (IV) with α,α-bis(trimethylsilyl)-1-butylketimine in the presence of a Lewis acid such as zinc dibromide for example or by reaction of a compound of general formula (VI)

(VI)

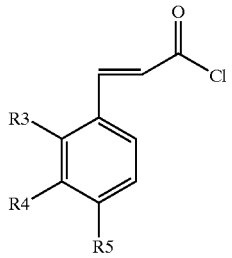

wherein $R_3$, $R_4$ and $R_5$ have the same meaning as that indicated above for the general formula (I), with trimethylaluminium in the presence of aluminium trichloride.

The reaction is carried out in a suitable solvent such as, for example, an alcohol such as methanol or ethanol, a halogenated hydrocarbon such as carbon tetrachloride, chloroform or dichloromethane, an ether such as tetrahydrofuran, ethyl ether, dioxane or dimethoxyethane, water or a mixture thereof. The reaction temperature can vary between −60° C. and the reflux temperature of the solvent and the reaction times can vary between two hours and several days.

Method E-4

The preparation of compounds of general formula (II), wherein $R_1$ and $R_2$ represent a hydrogen atom and $R_3$, $R_4$ and $R_5$ have the same meaning as that indicated above for the compounds of general formula (I), are carried out following different methods among which can be found, for example, the Wittig-Homer reaction with a benzaldehyge of general formula IV and then reducing the unsaturated α,β ester with a metal hydride such as diisobutylaluminum hydride (Dibal); by reaction of a benzaldehyde of general formula IV with α,α-bis(trimethylsilyl)-t-butylacetaldimine in the presence of a Lewis acid as zinc dibromide or by condensation of a benzaldehyde of general formula IV with acetaldehyde in the presence of a alkaline metal hydroxide such as sodium hydroxide or potassium hydroxide.

Method F

The preparation of the compounds of general formula (I), wherein $R_1$, $R_2$, $R_3$, $R_4$, $R_7$ and $R_8$ have the same meaning as that indicated above and $R_5$ represents a hydrogen, chlorine, fluorine atom, a methyl, trifluoromethyl, methoxy or trifluoromethoxy group, provided—in all cases—that $R_6$ represents an acetylaminosulphonyl group, or $R_6$ represents a hydrogen, chlorine, fluorine atom, a methyl, trifluoromethyl, methoxy or trifluoromethoxy group, provided—in all cases—that $R_5$ represents an acetylaminosulphonyl group, is carried out by reacting a compound of general formula (I) wherein $R_1$, $R_2$, $R_3$, $R_4$, $R_7$ and $R_8$ have the same meaning as that indicated above and $R_5$ represents a hydrogen, chlorine, fluorine atom, a methyl, trifluoromethyl, methoxy or trifluoromethoxy group, provided—in all cases—that $R_6$ represents an aminosulphonyl group, or $R_6$ represents a hydrogen, chlorine, fluorine atom, a methyl, trifluoromethyl, methoxy or trifluoromethoxy group, provided, in all cases, that $R_5$ represents an aminosulphonyl group, with a suitable reactant such as, for example, acetyl chloride or acetic anhydride. The reaction is carried out in the absence of solvent, or in a suitable solvent such as, for example, dimethylformamide or pyridine The most suitable temperatures vary between 0° C. and the reflux temperature and the reaction times lie between 15 minutes and 14 hours.

The invention provides pharmaceutical compositions that comprise, as well as a pharmaceutically acceptable excipient, at least one compound of general formula (I) or a physiologically acceptable salt thereof. The invention also relates to use of a compound of general formula (I) and its physiologically acceptable salts in the preparation of a medicament for the treatment of inflammation and/or for the treatment of other disorders associated with inflammation.

In the following examples the preparation of novel compounds is indicated in accordance with the invention. Some typical forms of use are also disclosed for different fields of application, as well as pharmaceutical formulae applicable to the compounds object of the invention. The examples that are indicated below, given by way of illustration, should not in any way limit the scope of the invention.

EXAMPLE 1

(Entry 1 of the Tables)

1-(4-Aminosulphonylphenyl)-4,5-dihydro-5-(4-metylphenyl)-3-trifluoromethyl-1H-pyrazole

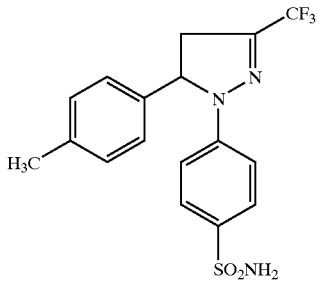

Preparation of (E)-1,1,1-trifluoro-4-(4-methylphenyl)-3-butene-2-one (Method E-1)

Into a flask with dry inert atmosphere, 15 ml of anhydrous THF is introduced and the flask cooled to −70° C. A solution of 2 M LDA in THF-hexane (5 ml, 10 mmoles) and diethylmethyl phosphonate (0.75 ml, 5 mmoles) dissolved in 5 ml of THF are added and the flask shaken for 30 minutes. Then, N-phenyltrifuoroacetimidoyl chloride (1.04 g, 5 mmoles) is added dropwise, (prepared according to Tamura, K.; Mizukami, H. et al.; J. Org. Chem., 1993, 58, 32–35) while continuing the shaking in the same conditions for 1 hour. P-tolualdehyde (0.6 g, 5 mmoles) is added, the cold bath removed and the flask left with shaking at room temperature for 16 hours. 10 ml of 2N HCl are added with shaking for a further 4 hours. The THF is eliminated with a rotavapor, the mixture extracted with ethyl ether (3×20 ml) and the combined organic extracts washed with 5% sodium bicarbonate solution and with saturated sodium chloride solution until reaching a pH—6 The mixture is dried over anhydrous sodium sulphate and evaporated. The crude oil obtained is purified using column chromatography through silica gel under pressure (eluting with AcOEt-petrol ether 1:9) to obtain (E)-1,1,1-trifluoro-4-(4-methylphenyl)-3-butene-2-one (0.8 g, yield: 75%) in the form of a clear oil.

IR (film, $cm^{-1}$): 1715, 1601, 1201, 1183, 1145, 1056, 811, 703

$^1$H-NMR ($CDCl_3$): δ2.4 (s, 3H), 6.97 (d, J=18 Hz, 1H); 7.25 (d, J=9 Hz, 2H); 7.54 (d, J=9 Hz, 2H); 7.95 (d, J=18 Hz, 1H).

Thin layer chromatography (TLC) (Petrol ether): Rf=0.16

Preparation of 1-(4-aminosulphonylphenyl)-4,5-dihydro-5-(4-methylphenyl)-3-trifluoromethyl-1H-pyrazole (METHOD A)

A solution of 4-(aminosulphonyl)phenylhydrazine chlorohydrate (0.82 g, 3.69 mmoles) and (E)-1,1,1-trifluoro-4-(4-methylphenyl)-3-butene-2-one (0.79 g, 3.69 mmoles) in 15 ml of acetic acid is refluxed for 3 hours under a nitrogen atmosphere. It is cooled, poured over water and extracted with AcOEt. The organic solution is washed with water, dried over anhydrous sodium sulphatic and evaporated to dryness under vacuum. The crude product thus obtained is crystallised from EtOH-petrol ether to give 1-(4-aminosulphonylphenyl)-4,5-dihydro-5-(4-methylphenyl)-3-trifluoromethyl-1H-pyrazole (0.65 g, yield: 45%).

m.p.=140–3° C.

IR(KBr, $cm^{-1}$): 3356, 3268, 1594, 1326, 1170, 1139, 1120, 1097.

$^1$H-NMR ($CDCl_3$): δ2.34 (s, 3H), 2.99–3.06 (dd, J=6.9 y 14 Hz; 1H); 3.66–3.73 (dd, J=12.6 and 14 Hz, 1H); 4.69 (broad s, 2H); 5.38–5.45 (dd, J=6.9 and 12.6 Hz, 1H); 7.04–7.11 (2d, J=8.1 y 9.3 Hz, 4H); 7.17 (d, J=8.1 Hz, 2H); 7.70 (d, J=9.3 Hz, 2H).

$^{13}$C-NMR ($CDCl_3$): 20.9; 41.2; 64.5; 113.4; 120.5 (q, J=268 Hz); 125.3, 127.6, 130.1; 133.2; 136.7; 138.3; 138.8 (q, J=38 Hz); 146.0.

TLC (AcOEt): Rf=0.89

EXAMPLE 2

(Entry 2 in the Tables)

1-(4-Aminosulphonylphenyl)-4,5-dihydro-5-phenyl-5-methyl-3-trifluoromethyl-1H-pyrazole

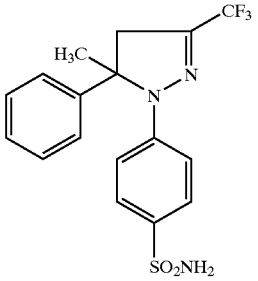

Preparation of (E)-1,1,1-trifluoro-4-methyl-4-phenyl-3-butene-2-one (METHOD E-2)

To a solution of boron dimethyl-trifluoro sulphide (3.9 g, 30 mmoles) in 75 ml of dichloromethane cooled to −60° C. trifluoroacetic anhydride (6.3 g, 30 mmoles) is added slowly. The mixture is shaken for 10 minutes and a solution of α-methylstyrene (3.54 g, 30 mmoles) in 15 ml de dicloromethane added slowly, maintaining the temperature at −60° C. Then the temperature is allowed to rise to −50° C., and kept at this value for 15 minutes, then allowed to rise to 0° C. and the mixture shaken under these conditions for 30 minutes. 50 ml of ethyl ether and 50 ml of an aqueous solution of 10% sodium bicarbonate solution are added. The phases are separated and the aqueous phase washed with more ether. The combination of the ether phases is washed with water, dried over anhydrous sodium sulphate and evaporated to dryness with a rotavapor The crude product thus obtained is purified using column chromatography through silica gel under pressure eluting with petrol ether. 2.0 g (51%) of unreacted starting α-methylstyrene and 2.35 g of (E)-1,1,1-trifluoro-4-phenyl-3-butene-2-one (yield 75%) were recovered in the form of colourless oil.

IR (film, $cm^{-1}$): 1709, 1596, 1204, 1142, 1072.

$^1$H-NMR ($CDCl_3$): δ2.71 (s, 3H), 6.8 (s, 1H), 7.45 (m, 3H), 7.6 (m, 2H).

Preparation of 1-(4-aminosulphonylphenyl)-4,5-dihydro-5-phenyl-5-methyl-3-trifluoro methyl-1H-pyrazole (METHOD A)

In a flask with an inert atmosphere (E)-1,1,1-trifluoro-4-methyl-4-(4-methylphenyl)-3-butene-2-one (1.75 g, 8.2 mmoles), 4-(aminosulphonyl)phenylhydrazine chlorohydrate (2 g, 9 mmoles) and piperidine (0.85 g, 10 mmoles) are added, dissolved in 100 ml of ethanol, and heated under reflux for 5.5 hours. The mixture is cooled, the solvent eliminated with a rotavapor, water added to the residue and the solution extracted with AcOEt. The organic phase is washed with water, dried over anhydrous sodium sulphate and evaporated to dryness. The crude product is purified using column chromatography through silica gel under pressure, eluting with AcOEt-petrol ether (4:6) obtaining 1-(4-aminosulphonylphenyl)-4,5-dihydro-5-phenyl-5-methyl-3-trifluoromethyl-1H-pyrazole in the form of a white solid (1.46 g, yield: 47%) with a m.p.=60–6° C.

IR (KBr, $cm^{-1}$): 3384, 3266, 1593, 1498, 1327, 1151, 1099, 703.

$^1$H-NMR ($CDCl_3$): δ1.6 (s, 3H); 2.8 (m, 1H); 3.1 (m, 1H); 4.5 (broad s, 2H), 7.2 (m, 3H), 7.4–7.55 (m, 4H); 7.7 (d, 2H).

$^{13}$C-NMR ($CDCl_3$): 27.6; 54.2; 63.1; 114.6; 124.0 (q, J=268 Hz); 125.6, 127.4, 127.8; 129.1; 131.0; 142.0 (q, J=38 Hz); 142.6; 147.5.

EXAMPLE 3

(Entry 3 in the Tables)

1-(4-aminosulphonylphenyl)-5-(2,4-difluorophenyl)-4,5-dihydro-3-trifluoro methyl-1H-pyrazole

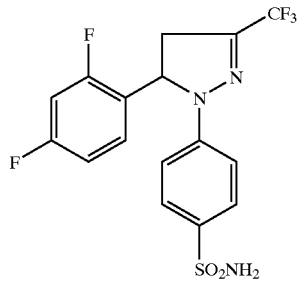

Preparation (E)-1,1,1-trifluoro-4-(2,4-difluorophenyl)-3-butene-2-one (METHOD E-3)

In a flask 2,4-difluorobenzaldehyde (20 g, 0.14 moles), glacial acetic acid (12.2 g, 0.2 moles) and piperidine (12.2 g, 0.14 moles) are dissolved in THF (300 ml). The solution is cooled to 5–10° C. and $CF_3COCH_3$ (8 g, 0.07 moles) bubbled through it. It is removed from the cold bath, the temperature increased to room temperature and the mixture kept at this temperature for 1.5 hours with continuous shaking. $CF_3COCH_3$ (5 g, 0.045 moles) is added once again and the mixture left for 1.5 hours with shaking. Once again 5 g is added and the mixture shaken for a further 1.5 hours. This step is repeated until a total of 35 g (0.31 moles) of $CF_3COCH_3$ have been added. A solution of 20% (50 ml) is added and the solvent eliminated under reduced pressure. 50 ml of water are added and the solution extracted with AcOEt. The organic phase is washed with water, 5% $H_2SO_4$, water and the mixture dried over anhydrous sodium sulphate. The solution is filtered and evaporated. The resulting crude product is distilled, obtaining 18.1 g of (E)-1,1,1-trifluoro-4-(2,4-difluorohphenyl)-3-butene-2-one with a m.p. of 50–1° C.

IR (KBr, $cm^{-1}$): 1717, 1602, 1583, 1277, 1146, 1059, 706

$^1$H-NMR ($CDCl_3$): δ6.9 (m, 2H); 7.05 (d, J=16 Hz, 1H); 7.6 (m, 1H); 8.0 (d, J=16 Hz, 1H).

Preparation of 1-(4-aminosulphonylphenyl)-5-(2,4-difluorophenyl)-4,5-dihydro-3-trifluoromethyl-1H-pyrazole (METHOD A)

A solution of 4-(aminosulphonyl)phenylhydrazine chlorohydrate (47.8 g, 0.21 moles) and (E)-1,1,1-trifluoro-4-(2,4-difluorophenyl)-3-butene-2-one (53.1 g of 95%, 0.21 moles) in 315 ml of acetic acid is refluxed for 24 hours under a nitrogen atmosphere. The mixture is cooled, poured over water and filtered. It is washed with toluene and the crude product thus obtained crystallised from isopropanol. 46.2 g are obtained. The mother waters of crystallisation from crystallisation, once concentrated, give another 12.6 g of product. In total 58.8 g (68%) of 1-(4-aminosulphonylphenyl)-5-(2,4-difluorophenyl)4,5-dihydro-3-trifluoromethyl-1H-pyrazole with a melting point of 160–2° C.

The following procedure can also be followed:

In a flask with an inert atmosphere sodium ethoxide (0.53 g, 7.72 mmoles) is dissolved in 45 ml of ethanol. 1,1,1-trifluoro-4-(2,4-difluorophenyl)-3-butene-2-one (prepared according to method E-1) (0.913 g, 3.86 mmoles) and 4-(aminosulphonyl)phenylhydrazine chlorohydrate (0.87 g, 3.87 mmoles) are added and the mixture was refluxed for 16 hours. The mixture was cooled, evaporated to dryness, cold water added, and the mixture acidified by adding acetic acid and the precipitated solid filtered. This solid was redissolved in ether, treated with active C, filtered and the solvent eliminated with a rotavapor. The resulting residue was crystallised from ethyl ether-petrol ether (50:50) to give 1-(4-aminosulphonylphenyl)-5-(2,4-difluorophenyl)-4,5-dihydro-3-trifluoromethyl-1H-pyrazole (1.02 g, yield: 65%) in the form of a solid m.p.=160–2° C.

IR (KBr, $cm^{-1}$): 3315, 3232, 1617, 1593, 1506, 1326, 1179, 1099, 1067.

$^1$H-NMR ($CDCl_3$): δ3.0 (dd, J=6.3 and 11.4 Hz, 1H); 3.80 (dd, J=11.4 and 12.6 Hz, 1H); 4.79 (broad s, 2H); 5.70 (dd, J=6.3 and 12.6 Hz, 1H); 6.8–6.95 (mm, 2H); 7.01–7.09 (m, 3H); 7.74 (d, J=8.7 Hz, 2H).

EXAMPLE 4

(Entry 4 of the Tables)

4,5-dihydro-1-(4-methylphenyl)-5-(4-methylsulphonylphenyl)-3-trifluorometyl-1H-pyrazole (METHOD A)

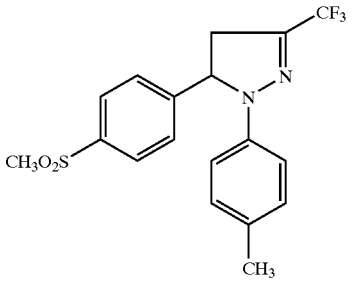

In a flask with an inert atmosphere (E)-1,1,1-trifluoro-4-(4-methylsulphonylphenyl)-3-butene-2-one (prepared according to the method E-1) (1.83 g, 6.58 mmoles) and 4-methylphenylhydrazine chlorohydrate (1.04 g, 6.58 mmoles) are dissolved in 50 ml de ethanol. A few drops of hydrochloric acid are added, and the mixture refluxed under an inert atmosphere for 4 days. The mixture is cooled and the product crystallised. The solution is filtered and the product recrystallised from ethanol. 4,5-dihydro-1-(4-methylphenyl]-5-(4-methylsulphonylphenyl)-3-trifluoromethyl-1H-pyrazole (0.8 g, yield: 32%) is obtained in the form of a solid with a melting point of 140–3° C.

IR (KBr, $cm^{-1}$): 1516, 1310, 1148, 1131, 1060, 774

$^1$H-NMR ($CDCl_3$): δ2.2 (s, 3H); 2.9(dd, J=7.8, 17.1 Hz, 1H); 3.05(s, 3H); 3.7(dd, J=12.9, 17.1 Hz, 1H); 5.45(dd,

J=7.8, 12.9 Hz, 1H); 6.8(d, J=8.4 Hz, 2H); 7.45(d, J=8.4 Hz, 2H), 7.9(d, J=8.4 Hz, 2H)

EXAMPLE 5

(Entry 39 in the Tables)

methyl 4,5-dihydro-5-(4-methylphenyl)-1-(4-methylsulphonylphenyl)-1H-pyrazole-3-carboxylate (METHOD B)

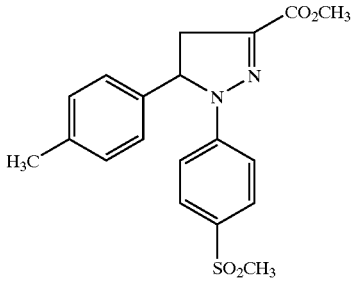

4,5-dihydro-5-(4-methylphenyl))-1-(4-methylsulphonylphenyl)-1H-pyrazole-3-carboxylic acid (6.9 g, 19.3 mmoles) and thionyl chloride (3.5 ml, 48 mmoles) are dissolved in 50 ml of tetrahydrofuran and the mixture shaken at room temperature for 16 hours. The mixture is evaporated to dryness with a rotavapor and the crude acid chloride so obtained is dissolved in 150 ml of methanol in a flask with inert atmosphere, and 8 ml (58 mmoles) of triethylamine added and the mixture shaken at room temperature for 2 hours. Water is added, the solid filtered and washed with abundant water and methanol. The desired methyl ester is thus obtained (5 8 g, yield: 82%) in the form of a cream coloured solid with a m.p.=155–160° C.

IR(KBr, $cm^{-1}$). 1741, 1561, 1260, 1226, 1135, 1089

$^1$H-NMR ($CDCl_3$): 2 3(s, 3H); 3(s, 3H); 3.1(dd, J=6, 18.3 Hz, 1H); 3.75(dd, J=12.6, 18.3 Hz, 1H); 5.4(dd, J=6, 12.6 Hz, 1H); 7–7.25(m, 6H); 7.7(d, J=8.7 Hz, 2H)

EXAMPLE 6

(Entry 41 in the Tables)

Preparation of 1-(4-aminosulphonylphenyl)-4,5-dihydro-5-(4-methylphenyl)-1H-pyrazole-3-carboxamide (METHOD C)

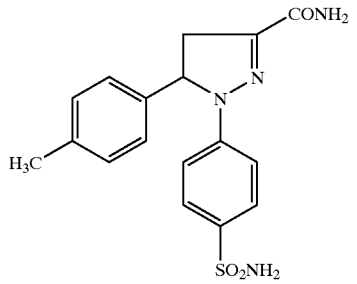

1-(4-aminosulphonylphenyl)-4,5-dihydro-5-(4-methylphenyl)-1H-pyrazole-3-carboxylic acid (3.7 g, 10.3 mmoles) and thionyl chloride (3 g, 25.8 mmoles) are dissolved in 70 ml of tetrahydrofuran and shaken at room temperature for 16 hours. The mixture is evaporated to dryness with a rotavapour and the crude acid chloride so obtained dissolved in 30 ml of methanol in a globe of inert atmosphere and cooled to 0° C. 9 ml of concentrated ammonium hydroxide solution dissolved in 20 ml of THF is added. The mixture is shaken at room temperature for 16 hours and the solvent eliminated with the rotavapor. Water is added to the residue and the mixture extracted with ethyl acetate, which is washed with water, dried over anhydrous sodium sulphate and evaporated to dryness. The crude residue so obtained is crystallised from ethyl acetate-petrol ether to give 2.6 g (yield: 72%) of the desired compound with a m.p.=210–5° C.

IR (KBr, $cm^{-1}$): 3450, 3337, 1656, 1596, 1345, 1141

$^1$H-NMR ($d_4$-$CH_3OH$): δ2.4(s, 3H); 3.05(dd, J=6, 17.7 Hz, 1H); 3.8(dd, J=12.9, 17.7 Hz, 1H); 5.6(dd, J=6, 12.9 Hz, 1H); 7.2–7.3(m, 6H); 7.75(d, J=8.7 Hz, 2H)

EXAMPLE 7

(Entry 43 in the Tables)

Preparation of 3-cyano-4,5-dihydro-5-(4-methylphenyl)-1-(4-methyl sulphonylphenyl)-1H-pyrazole (METHOD D)

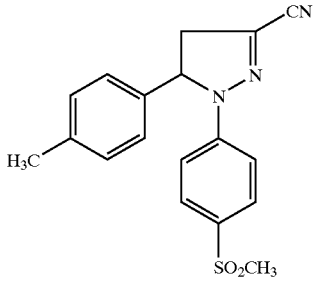

In a flask with inert atmosphere 6.3 ml of anhydrous DMF is placed, the flask cooled to 0° C. and 2.1 ml of thionyl chloride slowly added. The flask is shaken for 2 hours in these conditions. A solution of 4,5-dihydro-5-(4-methylphenyl)-1-(4-methylsulphonylphenyl)-1H-pyrazole-3-carboxamide (3.8 g, 10.6 mmoles) in 30 ml of DMF is added and the mixture shaken for 5 hours at 0° C. and, then, for 16 hours at room temperature. The contents of the flask are poured onto ice and the solid precipitate filtered. 3.35 g (yield: 93%) of crude product are obtained which is crystallised from ethyl acetate giving a yellow solid with a m.p.=162–4° C.

IR (KBr, $cm^{-1}$): 2220, 1593, 1500, 1389, 1296, 1143

$^1$H-NMR ($CDCl_3$) δ2.3(s, 3H); 3–3.1(s+dd, 4H); 3.75 (dd, J=12.6, 18 Hz, 1H); 5.5(dd, J=6.3, 12.6 Hz, 1H); 7–7.2(m, 6H); 7.7(d, J=8.7 Hz, 2H)

EXAMPLE 8

(Entry 64 of the Tables)

1-(4-acetylaminosulphonylphenyl)-5-(2,4-difluorophenyl)-4,5-dihydro-3-trifluoromethyl-1H-pyrazole (METHOD F)

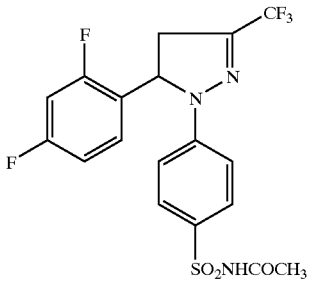

0.58 g (1.43 mmoles) of 1-(4-aminosulphonylphenyl)-5-(2,4-difluorophenyl)-4,5-dihydro-3-trifluoromethyl-1H-pyrazole and 2 ml acetyl chloride are heated under reflux for 2 hours. The mixture is cooled, evaporated to dryness under reduced pressure and the resulting residue dissolved in AcOEt, washed with water, dried over $Na_2SO_4$ and evaporated to dryness. 0.49 g (76%) of 1-(4-acetylaminosulphonylphenyl)-5-(2,4-difluorophenyl-4,5-dihydro-3-trifluoromethyl-1H-pyrazole were obtained in the form of a white solid with a m.p.=172–4° C.

IR (KBr, $cm^{-1}$) 3302, 1723, 1593, 1506, 1337, 1165

$^1$H-NMR ($CDCl_3$): δ2.0 (s, 3H), 3.0 (dd, J=6.6, 18.0 Hz, 1H); 3.8(dd, J=12.9, 18.0 Hz, 1H); 5.7(dd, J=6.6, 12.9 Hz, 1H); 6.9 (m, 2H); 7.05 (m+d, 3H); 7.85 (d, J=8.7 Hz, 2H); 8.1 (s, 1H)

EXAMPLES 9 AND 10

(Entries 75 and 76 in the Tables)

(+)-1-(4-aminosulphonylphenyl)-5-(2,4-difluorophenyl)-4,5-dihydro-3-trifluoromethyl-1H-pyrazole y (−)-1-(4-amino sulphonylphenyl)-5-(2,4-difluorophenyl)-4,5-dihydro-3-trifluoro methyl-1H-pyrazole

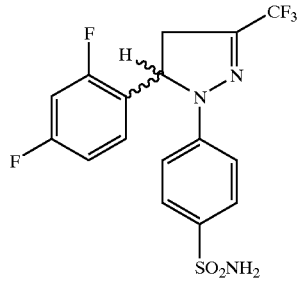

The racemic mixture (±)-1-(4-aminosulphonylphenyl)-5-(2,4-difluorophenyl)-4,5-dihydro-3-trifluoromethyl-1H-pyrazole is resolved into its enantiomers by high performance liquid chromatography using a CHIRALPAK AS column with 10μ particles and dimensions of 25×2 cm (Daicel), mobile phase 0.1% diethylamine in methanol and a flow rate of 8 ml/min. At a retention time of 7.4 minutes (+)-1 -(4-aminosulphonylphenyl)-5-(2,4-difluorophenyl)-4,5-dihydro-3-trifluoromethyl-1H-pyrazole is obtained as a white solid with a melting point of: 173–4° C.; enantiomeric purity 99.9% $[\alpha]_D$=+183.9 (c=1 $CH_3OH$) At a retention time of 9.2 minutes (−)-1-(4-aminosulphonylphenyl)-5-(2,4-difluorophenyl)-4,5-dihydro-3-trifluoromethyl-1H-pyrazole is obtained as a white solid with a m.p.: 173–4° C.; enantiomeric purity >99.9%, $[\alpha]_D$=−189.4 (c=1 $CH_3OH$).

Following the same procedure the examples corresponding to entries 77 and 78 in the tables are obtained.

Table 1 shows some examples that are encompassed by the general formula (I) and in Table 2 the data are indicated for identification of these compounds. The examples 1–36, 44–63 and 65–74 have been prepared according to method A, examples 37–39 according to method B, examples 40–42 according to method C, example 64 according to method F and the enantiomerically pure compounds 75–78 by resolution of the racemic mixture.

TABLE 1

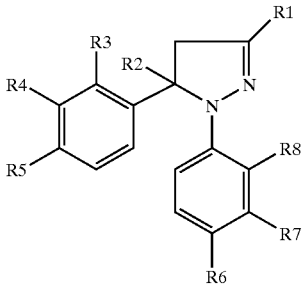

| Example | $R_1$ | $R_2$ | $R_3$ | $R_4$ | $R_5$ | $R_6$ | $R_7$ | $R_8$ |
|---|---|---|---|---|---|---|---|---|
| 1 | $CF_3$ | H | H | H | $CH_3$ | $SO_2NH_2$ | H | H |
| 2 | $CF_3$ | $CH_3$ | H | H | H | $SO_2NH_2$ | H | H |
| 3 | $CF_3$ | H | F | H | F | $SO_2NH_2$ | H | H |
| 4 | $CF_3$ | H | H | H | $SO_2CH_3$ | $CH_3$ | H | H |
| 5 | $CF_3$ | H | H | H | H | $SO_2NH_2$ | H | H |
| 6 | $CF_3$ | H | H | H | H | $SO_2CH_3$ | H | H |
| 7 | $CF_3$ | H | H | H | $CH_3$ | $SO_2CH_3$ | H | H |
| 8 | $CF_3$ | H | H | H | F | $SO_2NH_2$ | H | H |
| 9 | $CF_3$ | H | H | H | F | $SO_2CH_3$ | H | H |

TABLE 1-continued

| | | | | | | | | |
|---|---|---|---|---|---|---|---|---|
| 10 | $CF_3$ | H | H | H | $SO_2CH_3$ | F | H | H |
| 11 | $CF_3$ | H | H | F | F | $SO_2NH_2$ | H | H |
| 12 | $CF_3$ | H | Cl | H | Cl | $SO_2CH_3$ | H | H |
| 13 | $CF_3$ | H | Cl | H | Cl | $SO_2NH_2$ | H | H |
| 14 | $CF_3$ | H | $CH_3$ | H | H | $SO_2NH_2$ | H | H |
| 15 | $CF_3$ | H | H | $CH_3$ | H | $SO_2NH_2$ | H | H |
| 16 | $CF_3$ | H | F | H | H | $SO_2NH_2$ | H | H |
| 17 | $CF_3$ | H | F | H | H | $SO_2CH_3$ | H | H |
| 18 | $CF_3$ | H | H | F | H | $SO_2NH_2$ | H | H |
| 19 | $CF_3$ | H | H | F | H | $SO_2CH_3$ | H | H |
| 20 | $CF_3$ | H | H | H | $OCH_3$ | $SO_2NH_2$ | H | H |
| 21 | $CF_3$ | H | H | Cl | F | $SO_2NH_2$ | H | H |
| 22 | $CF_3$ | H | H | H | $OCF_3$ | $SO_2NH_2$ | H | H |
| 23 | $CF_3$ | H | F | F | H | $SO_2NH_2$ | H | H |
| 24 | $CF_3$ | H | $CH_3$ | H | $CH_3$ | $SO_2NH_2$ | H | H |
| 25 | $CF_3$ | H | H | F | F | $SO_2CH_3$ | H | H |
| 26 | $CH_3$ | H | H | H | F | $SO_2NH_2$ | H | H |
| 27 | $CH_3$ | H | H | H | F | $SO_2CH_3$ | H | H |
| 28 | $CH_3$ | H | H | H | $CH_3$ | $SO_2NH_2$ | H | H |
| 29 | $CH_3$ | H | H | H | $CH_3$ | $SO_2CH_3$ | H | H |
| 30 | $CH_3$ | H | H | H | $CF_3$ | $SO_2NH_2$ | H | H |
| 31 | H | H | H | H | H | $SO_2NH_2$ | H | H |
| 32 | H | H | H | H | H | $SO_2CH_3$ | H | H |
| 33 | $CH_3$ | H | H | H | $CF_3$ | $SO_2CH_3$ | H | H |
| 34 | $CO_2H$ | H | H | H | $CH_3$ | $SO_2NH_2$ | H | H |
| 35 | $CO_2H$ | H | H | H | H | $SO_2NH_2$ | H | H |
| 36 | $CO_2H$ | H | H | H | $CH_3$ | $SO_2CH_3$ | H | H |
| 37 | $CO_2CH_3$ | H | H | H | $CH_3$ | $SO_2NH_2$ | H | H |
| 38 | $CO_2CH_3$ | H | H | H | H | $SO_2NH_2$ | H | H |
| 39 | $CO_2CH_3$ | H | H | H | $CH_3$ | $SO_2CH_3$ | H | H |
| 40 | $CONH_2$ | H | H | H | H | $SO_2NH_2$ | H | H |
| 41 | $CONH_2$ | H | H | H | $CH_3$ | $SO_2NH_2$ | H | H |
| 42 | $CONH_2$ | H | H | H | $CH_3$ | $SO_2CH_3$ | H | H |
| 43 | CN | H | H | H | $CH_3$ | $SO_2CH_3$ | H | H |
| 44 | $CF_3$ | H | H | $CH_3$ | $CH_3$ | $SO_2NH_2$ | H | H |
| 45 | $CF_3$ | H | H | $CH_3$ | $OCH_3$ | $SO_2NH_2$ | H | H |
| 46 | $CF_3$ | H | H | F | $OCH_3$ | $SO_2NH_2$ | H | H |
| 47 | $CF_3$ | H | F | H | $OCH_3$ | $SO_2NH_2$ | H | H |
| 48 | $CF_3$ | H | $OCH_3$ | H | $OCH_3$ | $SO_2NH_2$ | H | H |
| 49 | $CF_3$ | H | $OCH_3$ | H | F | $SO_2NH_2$ | H | H |
| 50 | $CHF_2$ | H | $CH_3$ | H | $CH_3$ | $SO_2NH_2$ | H | H |
| 51 | $CF_3$ | H | F | F | F | $SO_2NH_2$ | H | H |
| 52 | $CF_3$ | H | Cl | H | F | $SO_2NH_2$ | H | H |
| 53 | $CF_3$ | H | F | H | $CF_3$ | $SO_2NH_2$ | H | H |
| 54 | $CF_3$ | H | $CF_3$ | H | $CF_3$ | $SO_2NH_2$ | H | H |
| 55 | $CF_3$ | H | $CH_3$ | F | H | $SO_2NH_2$ | H | H |
| 56 | $CF_3$ | H | $CH_3$ | H | $OCH_3$ | $SO_2NH_2$ | H | H |
| 57 | $CHF_2$ | H | F | H | F | $SO_2NH_2$ | H | H |
| 58 | $CF_3$ | H | $CF_3$ | H | F | $SO_2NH_2$ | H | H |
| 59 | $CF_3$ | H | H | H | $SO_2CH_3$ | F | H | F |
| 60 | $CF_3$ | H | Cl | H | H | $SO_2NH_2$ | H | H |
| 61 | $CF_3$ | H | F | H | Cl | $SO_2NH_2$ | H | H |
| 62 | $CF_3$ | H | $CH_3$ | H | F | $SO_2NH_2$ | H | H |
| 63 | $CF_3$ | H | F | H | $CH_3$ | $SO_2NH_2$ | H | H |
| 64 | $CF_3$ | H | F | H | F | $SO_2NHAc$ | H | H |
| 65 | $CF_3$ | H | H | H | $SO_2CH_3$ | Cl | H | H |
| 66 | $CF_3$ | H | H | H | $SO_2CH_3$ | H | H | H |
| 67 | $CF_3$ | H | H | H | $SO_2CH_3$ | H | H | F |
| 68 | $CF_3$ | H | H | H | $SO_2CH_3$ | Cl | H | $CH_3$ |
| 69 | $CF_3$ | H | H | H | $SO_2CH_3$ | H | F | H |
| 70 | $CF_3$ | H | H | H | $SO_2CH_3$ | H | $CH_3$ | H |
| 71 | $CF_3$ | H | H | H | $SO_2CH_3$ | $CH_3$ | H | $CH_3$ |
| 72 | $CF_3$ | H | H | H | $SO_2CH_3$ | H | H | Cl |
| 73 | $CF_3$ | H | H | H | $SO_2CH_3$ | H | H | $CH_3$ |
| 74 | $CF_3$ | H | H | H | $SO_2CH_3$ | Cl | H | Cl |

TABLE 1-continued

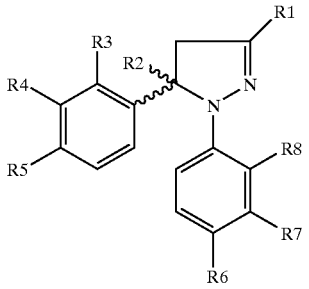

| Example | $R_1$ | $R_2$ | $R_3$ | $R_4$ | $R_5$ | $R_6$ | $R_7$ | $R_8$ | Enantiomeric Purity % | Specific rotation $[\alpha]_D$ |
|---|---|---|---|---|---|---|---|---|---|---|
| 75 | $CF_3$ | H | F | H | F | $SO_2NH_2$ | H | H | >99 | +183.9 (c = 1; $CH_3OH$) |
| 76 | $CF_3$ | H | F | H | F | $SO_2NH_2$ | H | H | >99 | −189.4 (c = 1; $CH_3OH$) |
| 77 | $CF_3$ | H | H | H | $SO_2CH_3$ | F | H | H | >99 | +181.2 (c = 1; $CH_3OH$) |
| 78 | $CF_3$ | H | H | H | $SO_2CH_3$ | F | H | H | >99 | −183.4 (c = 1; $CH_3OH$) |
| *79* | *$CF_3$* | *H* | *H* | *H* | *$SO_2CH_3$* | *H* | *H* | *$CF_3$* | | |

TABLE 2

| Example | m.p. ° C. | IR (KBr) $cm^{-1}$ | $^1$H-NMR ($CDCl_3$) δ ppm |
|---|---|---|---|
| 1 | 140–3 | 3356, 3268, 1594, 1326, 1170, 1139, 1120, 1097 | 2.34(s, 3H); 3(dd, J=6.9, 14Hz, 1H); 3.7(dd, J=12.6, 14Hz, 1H); 4.7(broad s, 2H); 5.4(dd, J=6.9, 12.6Hz, 1H); 7.1(2 d, J=8.1, 9.3Hz, 4H); 7.2(d, J=8.1Hz, 2H); 7.7(d, J=9.3Hz, 2H) |
| 2 | 60–6 | 3384, 3266, 1593, 1498, 1327, 1151, 1099, 703 | 1.6(s, 3H); 2.8(m, 1H); 3.1(m, 1H); 4.5(broad s, 2H); 7.2(m, 3H); 7.4–7.55(m, 4H); 7.7(d, 2H) |
| 3 | 160–2 | 3315, 3232, 1617, 1593, 1506, 1326, 1179, 1099, 1067 | 3(dd, J=6.3, 11.4Hz, 1H); 3.8(dd, J=11.4, 12.6Hz, 1H); 4.8(broad s, 2H); 5.7(dd, J=6.3, 12.6Hz, 1H); 6.8–6.95(m, 2H); 7–7.1(m, 3H); 7.7(d, J=8.7Hz, 2H) |
| 4 | 140–3 | 1516, 1310, 1148, 1131, 1060, 774 | 2.2(s, 3H); 2.9(dd, J=7.8, 17.1Hz, 1H); 3(s, 3H); 3.7(dd, J=12.9, 17.1Hz, 1H); 5.45(dd, J=7.8, 12.9Hz, 1H); 6.8(d, J=8.4Hz, 2H); 7(d, J=8.4Hz, 2H); 7.45(d, J=8.4Hz, 2H); 7.9(d, J=8.4Hz, 2H) |
| 5 | 156–7 | 3350, 3269, 1596, 1315 1188, 1142, 1101 | 3.04(dd, J=6.6, 18Hz, 1H); 3.7(dd, J=12.9, 18 Hz, 1H); 4.8(s, 2H); 5.45(dd, J=6.6, 12.9Hz, 1H); 7.0(d, J=9Hz, 2H); 7.2(d, J=6.6Hz, 2H); 7.3(m, 3H); 7.7(d, J=9Hz, 2H) |
| 6 | 137–40 | 1595, 1333, 1297, 1282, 1148, 771 | 3.0(s, 3H); 3.06(dd, J=6.6, 18Hz, 1H); 3.75(dd, J=12.8, 18.1H); 5.45(dd, J=6.6, 12.6Hz, 1H); 7.05(d, J=9Hz, 2H); 7.2(d, J=7.8Hz, 2H); 7.4(m, 3H); 7.7(d, J=9Hz, 2H) |
| 7 | 115–19 | 1592, 1332, 1148, 1133, 825, 775 | 2.3(s, 3H); 3.0(s, 3H); 3.05(dd, J=6.6, 19Hz, 1H) 3.7(dd, J=12.6, 19.1H); 5.4(dd, J=6.6, 12.6 Hz, 1H); 7.1(2d, J=8.1, 8.7Hz, 4H); 7.2(d, J=8.1 Hz, 2H); 7.7(d, J=8.7Hz, 2H) |
| 8 | 154–6 | 3337, 3254, 1594, 1510, 1324, 1158, 740 | 3.0(dd, J=6.6, 18Hz, 1H); 3.7(dd, J=12.6, 18Hz, 1H); 4.8(s, 2H); 5.4(dd, J=6.6, 12.6Hz, 1H); 7.1(m, 4H); 7.2(m, 2H); 7.7(d, J=9Hz, 2H) |
| 9 | 121–22 | 1592, 1509, 1148, 1120, 774 | 3.0(s, 3H); 3.05(dd, J=6.6, 17.4Hz, 1H); 3.7(dd, J=12.6, 17.4Hz, 1H); 5.4(dd, J=6.6 y 12.6Hz, 1H); 7.0(m, 4H); 7.2(m, 2H); 7.7(d, J=9Hz, 2H) |
| 10 | 103–5 | 1514, 1313, 1155, 1133, 1061, 827 | 2.9(dd, J=8.4, 17.4Hz, 1H); 3(s, 3H); 3.7(dd, J= 12.6, 17.4Hz, 1H); 5.4(dd, J=8.4, 12.6Hz, 1H); 6.9(m, 4H); 7.45(d, J=8.4Hz, 2H); 7.95(d, J=8.4 Hz, 2H) |
| 11 | 153–5 | 3318, 3250, 1596, 1323, 1135, 1066 | 3(dd, J=6.9 y 18Hz, 1H); 3.7(dd, J=12.6, 18Hz, 1H); 4.7(broad s, 2H); 5.4(dd, J=6.9, 12.6Hz, 1H); 7.0(m, 4H); 7.2(m, 1H); 7.7(d, J=9Hz, 2H) |
| 12 | 198–200 | 1596, 1320, 1303, 1138, 775 | 2.9–3.0(dd+s, 4H); 3.85(dd, J=12.6, 18.3Hz, 1H) 5.8(dd, J=6.6, 12.6Hz, 1H); 7.0(2 d, J=9Hz, 3H); 7.2(d, J=9Hz, 1H); 7.5(s, 1H); 7.8(d, J=9Hz, 2H) |

TABLE 2-continued

| Example | m.p. ° C. | IR (KBr) $cm^{-1}$ | $^1$H-NMR ($CDCl_3$) δ ppm |
|---|---|---|---|
| 13 | 143–5 | 3425, 3275, 1594, 1332, 1158, 1111, 825 | 2.95(dd, J=6.3, 18.3Hz, 1H); 3.8(dd, J=12.3, 18.3Hz, 1H); 4.8(s, 2H); 5.8(dd, J=6.3, 12.3Hz, 1H); 7.0(2 d, 3H); 7.2(d, J=8.7Hz, 1H); 7.5(s, 1H); 7.7(d, J=8.1Hz, 2H) |
| 14 | 124–6 | 3370, 3240, 1595, 1331, 1154, 1103 | ($d_6$-DMSO), 2.4(s, 3H); 2.9(dd, J=6.3, 18Hz, 1H); 3.9(dd, J=13.2, 18Hz, 1H); 5.9(dd, J=6.3, 13.2Hz 1H); 6.8(broad s, 1H); 7.0(d, J=9Hz, 2H); 7.1 (m, 3H); 7.2(t, 1H); 7.25(d, 1H); 7.6(d, J=9Hz, 2H) |
| 15 | 125–8 | 3370, 3265, 1595, 1329, 1158, 1066 | ($d_6$-DMSO), 2.3(s, 3H); 3(dd, J=6.3, 18.3Hz, 1H) 3.9(dd, J=12.6, 18.3Hz, 1H); 5.7(dd, J=6.3, 12.6Hz, 1H); 7–7.15(m, 5H); 7.25(t, 1H); 7.6(d, J=9Hz, 2H) |
| 16 | 166–8 | 3330, 3239, 1597, 1334, 1122, 769 | 3.05(dd, J=6.3, 17.7Hz, 1H); 3.7(dd, J=12.6, 17.7Hz, 1H); 5.7(dd, J=6.3, 12.6Hz, 1H); 7–7.2(m, 5H); 7.3(m, 1H); 7.7(d, J=9Hz, 2H) |
| 17 | 117–121 | 1594, 1304, 1150, 1119, 776 | 3(s, 3H); 3.05(dd, J=6.6, 17.1Hz, 1H); 3.8(dd, J=12.9, 17.1Hz, 1H); 5.75(dd, J=6.6, 12.9Hz, 1H); 7–7.2(m, 5H); 7.3(m, 1H); 7.75(d, J=9Hz, 2H) |
| 18 | 132–3 | 3323, 3249, 1596, 1323, 1179, 1131, 741 | 3(dd, J=7.2, 16.8Hz, 1H); 3.75(dd, J=12.9, 16.8Hz, 1H); 4.8(broad s, 2H); 5.4(dd, J=7.2, 12.9Hz, 1H); 6.9(d, J=9Hz, 1H); 7.05(m, 4H); 7.4(m, 1H); 7.7(d, J=9Hz, 2H) |
| 19 | 149–151 | 1593, 1296, 1144, 965, 789 | 3(s+dd, 4H); 3.75(dd, J=12.6, 13.8Hz, 1H); 5.4(dd, J=6.9, 12.6Hz, 1H); 6.9–7.1(m, 5H); 7.4(m, 1H); 7.7(d, J=9Hz, 2H) |
| 20 | 125–8 | 3336, 3254, 1593, 1329, 1156, 1112, 834 | 3(dd, J=6.6, 18Hz, 1H); 3.7(s+dd, 4H); 4.75(broad s, 2H); 5.4(dd, J=6.6, 12.9Hz, 1H); 6.9(d, J=8.4Hz, 2H); 7.05(d, J=8.4Hz, 2H); 7.1(d, J=8.4Hz, 2H); 7.7(d, J=8.4Hz, 2H) |
| 21 | 171–3 | 3376, 3239, 1593, 1500, 1328, 1153 | 3(dd, J=6.9, 18.3Hz, 1H); 3.75(dd, J=12.6, 18.3Hz, 1H); 4.7(broad s, 2H); 5.4(dd, J=6.9, 12.6Hz, 1H); 7–7.2(m, 4H); 7.3(m, 1H); 7.7(d, J=8.7Hz, 2H) |
| 22 | 134–7 | 3386, 3265, 1595, 1259, 1159 | ($d_6$-DMSO): 3(dd, J=6, 18.3Hz, 1H); 3.9(dd, J=12.9, 18.3Hz, 1H); 5.9(dd, J=6, 12.9Hz, 1H); 7.05(d, J=8.7Hz, 2H); 7.1(broad s, 2H); 7.4(s, 4H); 7.6(d, J=8.7Hz, 2H) |
| 23 | 152–4 | 3334, 3237, 1595, 1331, 1128, 831 | 3.05(dd, J=6.6, 18.6Hz, 1H); 3.8(dd, J=12.9, 18.6Hz, 1H); 4.7(broad s, 2H); 5.7(dd, J=6.6, 12.9Hz, 1H); 6.8(m, 1H); 7–7.2(m, 4H); 7.7(d, J=7.8Hz, 2H) |
| 24 | 158–160 | 3361, 3270, 1593, 1325, 1168, 1140, 821 | 2.3(s, 3H); 2.4(s, 3H); 2.9(dd, J=6.9, 17.7Hz, 1H); 3.8(dd, J=12.9, 17.7Hz, 1H); 4.7(broad s, 2H); 5.6(dd, J=6.9, 12.9Hz, 1H); 6.8–7.0(m, 4H); 7.1(s, 1H); 7.7(d, J=8.4Hz, 2H) |
| 25 | 132–5 | 1595, 1325, 1281, 1135, 774 | 3(s+dd, 4H); 3.8(dd, J=6.6, 18Hz, 1H); 5.45(dd, J=12.6, 18Hz, 1H); 6.9–7.05(m, 4H); 7.2(m, 1H); 7.75(d, J=9Hz, 2H) |
| 26 | 206–8 | 3329, 3215, 1593, 1509, 1333, 1155, 817 | ($d_6$-DMSO): 2(s, 3H); 2.65(dd, J=5.6, 20Hz, 1H); 3.55(dd, J=12.6, 20Hz, 1H); 5.35(dd, J=5.6, 12.6Hz, 1H); 6.8(d, J=8.4Hz, 2H); 6.95(s, 2H); 7.1–7.25(m, 4H); 7.5(d, J=8.4Hz, 2H) |
| 27 | 120–3 | 1590, 1508, 1293, 1141 | 2.1(s, 3H); 2.7(dd, J=6, 18.3Hz, 1H); 2.95(s, 3H); 3.5(dd, J=12, 18.3Hz, 1H); 5.1(dd, J=6, 12Hz, 1H); 6.9(d, J=9Hz, 2H); 7(m, 2H); 7.2(m, 2H); 7.6(d, J=9Hz, 2H) |
| 28 | 195–7 | 3300, 3210, 1594, 1509, 1330, 1157 | ($d_4$-$CH_3OH$): 2(s, 3H); 2.2(s, 3H); 2.6(dd, J=5.4, 17.7Hz, 1H); 3.5(dd, J=11.7, 17.7Hz, 1H); 5.3(dd, J=5.4, 11.7Hz, 1H); 6.8(d, J=8.7Hz, 2H); 6.9(s, 2H); 7.1(m, 4H); 7.5(d, J=8.7Hz, 2H) |
| 29 | 113–7 | 1592, 1509, 1298, 1142, 771 | 2.1(s, 3H); 2.3(s, 3H); 2.7(dd, J=6.3, 20Hz, 1H); 2.95(s, 3H); 3.5(dd, J=13, 20Hz, 1H); 5.1(dd, J=6.3, 13Hz, 1H); 6.9(d, J=9Hz, 2H); 7.1(m, 4H); 7.6(d, J=9Hz, 2H) |
| 30 | 190–4 | 3344, 3263, 1596, 1329, 1155, 616 | ($d_4$-$CH_3OH$): 2.9(dd, J=6, 18.3Hz, 1H); 3.7(dd, J=12, 18.3Hz, 1H); 5.3(dd, J=6, 12Hz, 1H); 7.1(m, 3H); 7.4(m, 5H); 7.7(d, J=8.7Hz, 2H) |
| 31 | 206–8 | 1595, 1290, 1144, 774 | 2.9(s+dd, 4H); 3.6(dd, J=12.3, 18.3Hz, 1H); 5.1(dd, J=6.3, 12.3Hz, 1H); 6.9(s, 1H); 7(d, J=9Hz, 2H); 7.3(m, 5H); 7.7(d, J=9Hz, 2H) |
| 32 | 197–202 | 3320, 3250, 1594, 1325, 1165 | ($d_6$-DMSO): 2(s, 3H); 2.7(dd, J=5.4, 18Hz, 1H); 3.6(dd, J=12, 18Hz, 1H); 5.5(dd, J=5.4, 12Hz, 1H); 6.85(d, J=8.1Hz, 2H); 7(s, 2H); 7.4(d, J=8.1Hz, 2H); 7.5(d, J=8.1Hz, 2H); 7.7(d, J=8.1Hz, 2H) |

TABLE 2-continued

| Example | m.p. ° C. | IR (KBr) $cm^{-1}$ | $^1$H-NMR ($CDCl_3$) δ ppm |
|---|---|---|---|
| 33 | 136–8 | 1595, 1512, 1325, 1141, 771 | 2.1(s, 3H); 2.7(dd, J=6.3, 19Hz, 1H); 3(s, 3H); 3.5(dd, J=12.6, 19Hz, 1H); 5.2(dd, J=6.3, 12.6Hz, 1H); 6.9(d, J=8.4Hz, 2H); 7.35(d, J=8.4Hz, 2H); 7.6(2 d, 4H) |
| 34 | 172–6 | 3304, 3237, 1706, 1326, 1138, | ($d_4$-$CH_3OH$): 2.35(s, 3H); 3.05(dd, J=6.6, 18.6Hz, 1H); 3.8(dd, J=12.6, 18.6Hz, 1H); 5.5(dd, J=6.6, 12.6Hz, 1H); 7.2(m, 6H), 7.7(d, J=9Hz, 2H) |
| 35 | 157–164 | 3247, 1700, 1595, 1333, 1150, 1098 | ($d_4$-$CH_3OH$): 3.1(dd, J=6, 18.3Hz, 1H); 3.9(dd, J=12.6, 18.3Hz, 1H); 5.7(dd, J=6, 12.6Hz, 1H); 7.2–7.5(m, 7H); 7.7(d, J=8.7Hz, 2H) |
| 36 | 202–5 | 1730, 1582, 1275, 1206, 1134, 1087 | ($d_6$-DMSO): 2.2(s, 3H); 2.8(dd, J=6.3, 18Hz, 1H); 3.05(s, 3H); 3.8(dd, J=12.6, 18Hz, 1H); 5.7(dd, J=6.3, 12.6Hz, 1H); 7.2(m, 6H); 7.7(d, J=9Hz, 2H); 13.2(broad s, 1H) |
| 37 | 192–7 | 3306, 3231, 1706, 1324, 1158 | 2.2(s, 3H); 3(dd, J=6.3, 18Hz, 1H); 3.2(broad s, 2H); 3.65(dd, J=12.6, 18Hz, 1H); 3.8(s, 3H); 5.4(dd, J=6.3, 12.6Hz, 1H); 7–7.1(m, 6H); 7.6(d, J=8.7Hz, 2H) |
| 38 | 84–90 | 3308, 3224, 1700, 1317, 1147, 1094 | ($d_4$-$CH_3OH$): 3.1(dd, J=6, 18.3Hz, 1H); 3.9(s+dd, 4H); 5.7(dd, J=6, 12.9Hz, 1H); 7.2–7.4(m, 7H); 7.75(d, J=8.7Hz, 2H) |
| 39 | 155–160 | 1741, 1561, 1260, 1226, 1135, 1089 | 2.3(s, 3H); 3(s, 3H); 3.1(dd, J=6, 18.3Hz, 1H); 3.75(dd, J=12.6, 18.3Hz, 1H); 5.4(dd, J=6, 12.6Hz, 1H); 7–7.25(m, 6H); 7.7(d, J=8.7Hz, 2H) |
| 40 | 200–5 | 3431, 3285, 1647, 1592, 1328, 1142 | ($d_4$-$CH_3OH$): 3.1(dd, J=6, 18.3Hz, 1H); 3.9 (dd, J=12.9, 18.3Hz, 1H); 5.7(dd, J=6, 12.9Hz, 1H); 7.2–7.5(m, 7H); 7.75(d, J=8.7Hz, 2H) |
| 41 | 210–5 | 3450, 3337, 1656, 1596, 1345, 1141 | ($d_4$-$CH_3OH$): 2.4(s, 3H); 3.05(dd, J=6, 17.7Hz, 1H); 3.8(dd, J=12.9, 17.7Hz, 1H); 5.6(dd, J=6, 12.9 Hz, 1H); 7.2–7.3(m, 6H) 7.75(d, J=8.7Hz, 2H) |
| 42 | 128–132 | 3440, 3200, 1680, 1590, 1135 | 2.3(s, 3H); 3(s, 3H); 3.1(dd, J=6.3, 18.6Hz, 1H); 3.8(dd, J=12.6, 18.6Hz, 1H); 5.4(dd, J=6.3, 12.6Hz, 1H); 5.6(broad s, 1H); 6.7(broad s, 1H); 7–7.2(m, 6H); 7.7(d, J=8.7Hz, 2H) |
| 43 | 162–4 | 2220, 1593, 1500, 1389, 1296, 1143 | 2.3(s, 3H); 3–3.1(s+dd, 4H); 3.75(dd, J=12.6, 18Hz, 1H); 5.5(dd, J=6.3, 12.6Hz, 1H); 7–7.2(m, 6H); 7.7(d, J=8.7Hz, 2H) |
| 44 | 152–5 | 3316, 3240, 1594, 1323, 1178, 1121, 1065, 549 | 2.2(s, 6H); 3(dd, J=6.3, 18.3Hz, 1H); 3.7(dd, J=12.6, 18.3Hz, 1H); 4.7(broad s, 2H); 5.4(dd, J=6.3, 12.6Hz, 1H); 6.95(s+d, J=7.8Hz, 2H); 7.1(2d, J=7.8, 8.7Hz, 3H); 7.7(d, J=8.7Hz, 2H) |
| 45 | 170–5 | 3360, 3267, 1595, 1507, 1329, 1255, 1159, 619 | 2.2(s, 3H); 3(dd, J=7.2, 18Hz, 1H); 3.6–3.8(s+dd, 4H); 4.6(broad s, 2H); 5.35(dd, J=7.2, 12.9Hz, 1H); 6.75(d, J=7.8Hz, 1H); 7(s+d, 2H); 7.1(d, J=8.7Hz, 2H); 7.7(d, J=8.7Hz, 2H) |
| 46 | 108–114 | 3383, 2270, 1595, 1519, 1329, 1277, 1160, 1066 | 3(dd, J=6.6 18.3Hz, 1H); 3.75(dd, J=12.3, 18.3 Hz, 1H); 3.9(s,3H); 5.4(dd, J=6.6, 12.3Hz, 1H); 6.95(m, 3H); 7.05(d, J=8.7Hz, 2H); 7.7(d, J=8.7Hz, 2H) |
| 47 | 157–9 | 3357, 3267, 1630 1595, 1508, 1330, 1264, 1158, 1066 | 3.05(dd, J=6.3, 18Hz, 1H); 3.7–3.8(s+dd, 4H); 4.8(broads, 2H); 5.7(dd, J=6.3, 12.9Hz, 1H); 6.6–6.7(m, 2H); 6.95(t, J=8.7Hz, 1H); 7.05(d, J=9Hz, 2H); 7.7(d, J=9Hz, 2H) |
| 48 | 121–6 | 3376, 3268, 1593, 1507, 1329, 1160 | 2.9(dd, J=6, 18Hz, 1H); 3.65(dd, J=12.6, 18Hz, 1H); 3.75(s, 3H); 3.85(s, 3H); 4.9(s, 2H); 5.65(dd, J=6, 12.6Hz, 1H); 6.35(d, J=8.7Hz, 1H); 6.5(s, 1H); 6.9(d, J=8.7Hz, 1H); 7(d, J=8.7Hz, 2H); 7.7(d, J=8.7Hz, 2H) |
| 49 | 179–82 | 3317, 3231, 1593, 1507, 1326, 1178 | ($d_6$-DMSO): 2.95(dd, J=5.4, 18Hz, 1H); 3.7–3.8(m, 4H); 5.8(dd, J=5.4, 12.6Hz, 1H); 6.7(dd, J=8.1, 10.5Hz, 1H); 6.9–7.1(m, 6H); 7.6(d, J=8.7Hz, 2H) |
| 50 | 181–3 | 3348, 3268, 1593, 1321, 1165 | 2.25(s, 3H); 2.35(s, 3H); 2.85(dd, J=6.9, 18Hz, 1H); 3.7(dd, J=12.6, 18Hz, 1H); 5.45(dd, J=6.9, 12.6Hz, 1H); 6.5(t, J=54Hz, 1H); 6.8–6.9(m, 4H); 7(s, 1H); 7.65(d, J=9Hz, 2H) |
| 51 | 159–61 | 3382, 3285, 1595, 1514, 1328, 1161 | 3(dd, J=6.3, 17.7Hz, 1H); 3.8(dd, J=12.6, 17.7Hz, 1H); 4.7(s, 2H); 5.7(dd, J=6.3, 12.6Hz, 1H); 6.8(m, 1H); 6.9(m, 1H); 7(d, J=9Hz, 2H); 7.75(d, J=9Hz, 2H) |
| 52 | 167–9 | 3318, 3239, 1593, 1503, 1492, 1321, 1068 | ($d_6$-DMSO): 3(dd, J=6.3, 18.3Hz, 1H); 3.95(dd, 12.9, 18.3Hz, 1H); 5.95(dd, J=6.3, 12.9Hz, 1H); 7(d, J=8.7Hz, 2H); 7.1–7.2(m, 4H); 7.55(d, J=8.4Hz, 1H); 7.65(d, J=8.7Hz, 2H) |
| 53 | 170–3 | 3425, 3284, 1595, 1330, 1138 | ($d_6$-DMSO): 3.2(dd, J=5.7, 18Hz, 1H); 3.9(dd, J=12.9, 18Hz, 1H); 6(dd, J=5.7, 12.9Hz, 1H); 7.1(m, 4H); 7.4–7.7(m, 4H); 7.8(d, J=10.8Hz, 1H) |

TABLE 2-continued

| Example | m.p. ° C. | IR (KBr) $cm^{-1}$ | $^1$H-NMR ($CDCl_3$) δ ppm |
|---|---|---|---|
| 54 | 212–4 | 3376, 3277, 1597, 1332, 1274, 1132 | 2.8(dd, J=6.3, 18.5Hz, 1H); 3.7(dd, J=13, 18.5Hz, 1H); 5.75(dd, J=6.3, 13Hz, 1H); 6.1(s, 2H); 6.8(d, J=8.5Hz, 2H); 7.2(d, J=8.3Hz, 1H); 7.6(d, J=8.5Hz, 2H); 7.65(d, J=8.3Hz, 1H); 7.9(s, 1H) |
| 55 | 193–5 | 3353, 3270, 1593, 1509, 1321, 1141 | ($d_6$-DMSO): 2.3(s, 3H); 2.9(dd, J=6.1, 12.2Hz, 1H); 3.95(dd, J=12.2, 12.9Hz, 1H); 5.95(dd, J=6.1, 12.9Hz, 1H); 6.65(s ancho, 1H); 7(d, J=8.8Hz, 2H); 7.1–7.2(m, 4H); 7.65(d, J=8.8Hz, 2H) |
| 56 | 148–50 | 3384, 3266, 1593, 1324, 1252, 1166 | 2.35(s, 3H); 2.9(dd, J=5.6, 18Hz, 1H); 3.7–3.8(m, 4H); 4.9(banda ancha, 2H); 5.5(dd, J=5.6, 12.6Hz, 1H); 6.6(dd, J=2.2, 8.5Hz, 1H); 6.8(s, 1H); 6.85–6.95(2d, 3H); 7.7(d, J=9Hz, 2H) |
| 57 | 157–60 | 3384, 3346, 3277, 3255, 1596, 1503, 1341, 1158 | 3(dd, J=6.1, 17.8Hz, 1H); 3.7(dd, J=12.4, 17.8Hz, 1H); 4.75(s, 2H); 5.6(dd, J=6.1, 12.4Hz, 1H); 6.5(t, J=54Hz, 1H); 6.8–7(m, 5H); 7.7(d, J=8.8Hz, 2H) |
| 58 | 174–7 | 3384, 3261, 1596, 1329, 1117 | 2.95(dd, J=5.6, 17.3Hz, 1H); 3.75(dd, J=12.4, 17.3Hz, 1H); 4.7(s ancho, 2H); 5.8(dd, J=5.6, 12.4Hz, 1H); 6.95(d, J=8.3Hz, 2H); 7.2(m, 2H); 7.5(d, J=7.5Hz, 1H); 7.75(d, J=8.3Hz, 2H) |
| 59 | 105–6 | 1596, 1510, 1314, 1264, 1150, 845 | 3(s+dd, 4H); 3.6 (dd, J=12.2, 17.6Hz, 1H); 5.6 (dd, J=6.2, 12.2Hz, 1H); 6.65 (t, J=9Hz, 1H); 6.75 (t, J=8Hz, 1H); 7.35 (m, 3H); 7.8 (d, J=8.3Hz, 2H) |
| 60 | 157–9 | 3354, 3268, 1594, 1325, 1122, 753 | 2.95(dd, J=6.6, 18.5Hz, 1H); 3.85(dd, J=12.7, 18.5Hz, 1H); 4.8(s, 2H); 5.8(dd, J=6.6, 12.7Hz, 1H); 6.9–7(m, 3H); 7.1–7.3(m, 2H); 7.45(d, J=7.8Hz, 1H); 7.7(d, J=8.6Hz, 2H) |
| 61 | 180–5 | 3407, 3295, 1593, 1334, 1161 | ($d_4$-$CH_3OH$): 3.2(dd, J=6.3, 18.1Hz, 1H); 3.95(dd, J=12.9, 18.1Hz, 1H); 6(dd, J=6.3, 12.9Hz, 1H); 7.2(d, J=8.8Hz, 2H); 7.3(m, 2H); 7.4(d, J=10.3Hz, 1H); 7.8(d, J=8.8Hz, 2H) |
| 62 | 154–60 | 3406, 3262, 1593, 1330, 1155 | 2.4(s, 3H); 2.9(dd, J=6.6, 17.8Hz, 1H); 3.75(dd, J=12.7, 17.8Hz, 1H); 4.8(s, 2H); 5.5(dd, J=6.6, 12.7Hz, 1H); 6.8–7(m, 5H); 7.7(d, J=8.8Hz, 2H) |
| 63 | 166–7 | 3430, 3298, 1593, 1508, 1334, 1161, 1123 | 2.3(s, 3H); 3(dd, J=6.3, 18.3Hz, 1H); 3.75(dd, J=12.7, 18.3Hz, 1H); 4.65(s, 2H); 5.7(dd, J=6.3, 12.7Hz, 1H); 6.85–7(m, 3H); 7.05(d, J=8.8Hz, 2H); 7.7(d, J=8.8Hz, 2H) |
| 64 | 172–4 | 3302, 1722, 1593, 1506, 1337, 1165 | 2(s, 3H); 3(dd, J=6.6, 18Hz, 1H); 3.8(dd, J=12.9, 18Hz, 1H); 5.7(dd, J=6.6, 12.9Hz, 1H); 6.8–6.95(m, 2H); 7–7.1(m, 3H); 7.85(d, J=8.7Hz, 2H); 8.1(s, 1H) |
| 65 | 117–21 | 1594, 1492, 1310, 1257, 1154, 1063 | 2.95(dd, J=7.3, 17.8Hz, 1H); 3(s, 3H); 3.7(dd, J=12.7, 17.8Hz, 1H); 5.45(dd, J=7.3, 12.7Hz, 1H); 6.8(d, J=8.8Hz, 2H); 7.1(d, J=8.8Hz, 2H); 7.4(d, J=8.3Hz, 2H); 7.9(d, J=8.3Hz, 2H) |
| 66 | 114–5 | 1598, 1503, 1275, 1156, 1079, 749 | 2.95(dd, J=7.6, 17.8Hz, 1H); 3(s, 3H); 3.7(dd, J=12.7, 17.8Hz, 1H); 5.45(dd, J=7.6, 12.7Hz, 1H); 6.9(m, 3H); 7.15(t, J=7.8Hz, 2H); 7.4(d, J=8.1Hz, 2H); 7.9(d, J=8.1Hz, 2H) |
| 67 | 98–9 | 1606, 1503, 1317, 1148, 1123, 762 | 3(s+dd, 4H); 3.65(dd, J=13.1, 17.1Hz, 1H); 5.8(dd, J=7.6, 13.1Hz, 1H); 6.9(m, 2H); 7(t, J=8.1Hz, 1H); 7.3(d, J=8.1Hz, 2H); 7.45(t, J=8.3Hz, 1H); 7.8(d, J=8.1Hz, 2H) |
| 68 | *104–8* | *1617, 1496, 1310, 1253, 1154, 1113, 809* | 2.3(s, 3H); 3(m, 4H); 3.5(dd, J=11.7, 17.1Hz, 1H); 5.45(t, J=11.7Hz, 1H); 6.75(d, J=8.5Hz, 1H); 7(d, J=8.5Hz, 1H); 7.1(s, 1H); 7.45(d, J=8Hz, 2H); 7.9(d, J=8Hz, 2H) |
| 69 | 116–7 | 1616, 1587, 1498, 1310, 1155, 828 | 2.9(dd, J=7.5, 16.8Hz, 1H); 3(s, 3H); 3.7(dd, J=12.7, 16.8Hz, 1H); 5.4(dd, J=7.5, 12.7Hz, 1H); 6.6(m, 2H); 6.7(d, J=11Hz, 1H); 7.1(dd, J=7.6, 14.9Hz, 1H); 7.4(d, J=8Hz, 2H); 7.9(d, J=8Hz, 2H) |
| 70 | 114–6 | 1597, 1315, 1149, 1072, 959, 789 | 2.25(s, 3H); 2.9(dd, J=7.6, 17.8Hz, 1H); 3(s, 3H); 3.7(dd, J=12.9, 17.8Hz, 1H); 5.45(dd, J=7.6, 12.9Hz, 1H); 6.6(d, J=7.8Hz, 1H); 6.7(d, J=7.8 Hz, 1H); 6.9(s, 1H); 7(t, J=7.8Hz, 1H); 7.45(d, J=8Hz, 2H); 7.9(d, J=8Hz, 2H) |
| 71 | 132–3 | 1601, 1509, 1314, 1154, 1113, 809 | 2.2(s, 3H); 2.3(s, 3H); 3(m, 4H); 3.5(dd, J=11.7, 16.6Hz, 1H); 5.4(t, J=11.7Hz, 1H); 6.8(m, 2H); 6.9(s, 1H); 7.5(d, J=8Hz, 2H); 7.85(d, J=8Hz, 2H) |
| 72 | | | 2.95(s, 3H); 3.15(dd, J=6.5, 17.8Hz, 1H); 3.65(dd, J=12.7, 17.8Hz, 1H); 5.95(dd, J=6.5, 12.7Hz, 1H); 6.95(d, J=7.8Hz, 1H); 7.1(t, J=7.3Hz, 1H); 7.2(m, 2H); 7.35(d, J=8.3Hz, 2H); 7.8(d, J=8.3Hz, 2H) |

TABLE 2-continued

| Example | m.p. ° C. | IR (KBr) $cm^{-1}$ | $^1$H-NMR ($CDCl_3$) δ ppm |
|---|---|---|---|
| 73 | | | 2.3(s, 3H); 3(s+dd, 4H); 3.5(dd, J=11.7, 17.8Hz, 1H); 5.5(1, J=11.7Hz, 1H); 6.85(d, J=7.8Hz, 1H); 7(m, 2H); 7.1(d, J=6.1Hz, 1H); 7.5(d, J=8.3Hz, 2H); 7.85(d, J=8.3Hz, 2H) |
| 74 | *103–6* | *1625, 1483, 1312, 1150, 1130, 819* | 3(s, 3H); 3.15(dd, J=5.9, 17.8Hz, 1H); 3.7(dd, J=11.7, 17.8Hz, 1H); 5.95(dd, J=5.9, 11.7Hz, 1H); 7.05(m, 2H); 7.2(s, 1H); 7.3(d, J=8.1Hz, 2H); 7.8(d, J=8.1Hz, 2H) |
| 75 | 173–4 | 3330, 3250, 1617, 1593, 1506, 1329, 1121, 1099, 855 | 3(dd, J=6.3, 11.4Hz, 1H); 3.8(dd, J=11.4, 12.6Hz, 1H); 4.8(s ancho, 2H); 5.7(dd, J=6.3, 12.6Hz, 1H); 6.8–6.95(m, 2H); 7–7.1(m, 3H); 7.7(d, J=8.7Hz, 2H) |
| 76 | 173–4 | 3330, 3250, 1617, 1593, 1506, 1329, 1121, 1099, 855 | 3(dd, J=6.3, 11.4Hz, 1H); 3.8(dd, J=11.4, 12.6Hz, 1H); 4.8(s ancho, 2H); 5.7(dd, J=6.3, 12.6Hz, 1H); 6.8–6.95(m, 2H); 7–7.1(m, 3H); 7.7(d, J=8.7Hz, 2H) |
| 77 | 113–5 | 1508, 1315, 1155, 1133, 1067, 831 | 2.9(dd, J=8.4, 17.4Hz, 1H); 3(s, 3H); 3.7(dd, J=12.6, 17.4Hz, 1H); 5.4(dd, J=8.4, 12.6Hz, 1H); 6.9(m, 4H); 7.45(d, J=8.4Hz, 2H); 7.95(d, J=8.4Hz, 2H) |
| 78 | 113–4 | 1508, 1315, 1155, 1133, 1067, 827 | 2.9(dd, J=8.4, 17.4Hz, 1H); 3(s, 3H); 3.7(dd, J=12.6, 17.4Hz, 1H); 5.4(dd, J=8.4, 12.6Hz, 1H); 6.9(m, 4H); 7.45(d, J=8.4Hz, 2H); 7.95(d, J=8.4Hz, 2H) |
| *79* | | *1603, 1318, 1148, 1060, 955, 760* | *3(s, 3H); 3.1(dd, J=8.8, 16.4Hz, 1H); 3.6(dd, J=12.7, 16.4Hz, 1H); 5.6(dd, J=8.8, 12.7Hz, 1H); 7(d, J=7.8Hz, 1H); 7.15(t, J=8.1Hz, 1H); 7.3(t, J=8.1Hz, 1H); 7.4(d, J=8.3Hz, 2H); 7.6(d, J=7.8Hz, 1H); 7.8(d, J=8.3Hz, 2H)* |

The products object of the invention are potent, orally active, anti-inflammatory agents, and selective inhibitors of COX-2, with a notable analgesic activity, lack ulcerogenic effects and are very active in the experimental arthritis test. With a view to demonstrating these activities, by way of example, some pharmacological assays are now indicated.

Inhibition of the Synthesis of Prostaglandins in Inflammatory Exudate and Mucus Membrane in Rat In this assay, as well as demonstrating the selective inhibition of COX-2, the anti-inflammatory activity is also demonstrated, along with the absence of effects on gastric prostaglandins, after oral administration. The assay was carried out by modification of a method described by O. Tofanetti et al. (Med. Sci. Res. 1989, 17, 745–746). The products under study are administered orally at an initial screening dose of 40 mg/kg One hour after treatment the rats were anaesthetised and a sponge soaked in carrageenan was implanted subcutaneously in the interscapular zone. Six hours after implantation the rats were sacrificed and the interscapular sponges extracted as well as gastric mucuous. Next the $PGE_2$ content was determined by immunoassay for each one of the samples, in the sponge exudate on the one hand and in the gastric mucus on the other. The inhibition of $PGE_2$ in the inflammatory exudate demonstrates anti-inflammatory activity, both of COX-2 and COX-1 inhibitors, whereas inhibition of $PGE_2$ in the gastric mucus is considered a COX-1 inhibitory effect.

Table 3 summaries the results obtained with the compound of examples 3 and in table 4 the ED-50 (effective dose-50) is shown, as well as its selectivity. It is a more potent anti-inflammatory that the reference product.

TABLE 3

COX-2/COX-1 activity in vivo

| | Inhibition of $PGE_2$ | |
|---|---|---|
| Product (Dose 40 mg/kg, po) | Inflammatory exudate | Gastric mucus |
| Example 3 | 92% | 0 |
| Meloxicam | 97% | 65% |
| Nabumetone | 93% | 0 |

TABLE 4

ED-50 of the COX-2/COX-1 activity in vivo

| | Inhibition of $PGE_2$ | |
|---|---|---|
| Product ED-50 (mg/kg, po) | Inflammatory exudate | Gastric mucus |
| Example 3 | 36 | >40 |
| Nabumetone | 110 | >40 |

Analgesic Activity Against "Hyperalgesia" by Thermal Stimulus of Pre-inflamed Rat Paw In this assay the analgesic activity in rat was monitored following the method described by K. Hargreaves et al. (Pain, 1988, 32, 77–78). Firstly, a suspension of carrageenan was injected into the back right paw of each rat. After two hours the products under study were administered orally at a screening dose of 40 mg/kg. Two hours after treatment a heat source was applied to the sole of each back paw of the rats and the time measured that they took to remove the paw measured. Hyperalgesia was determined by comparing the percentage of algesia of the paw injected with carrageenan to the other back paw. The analgesic activity was calculated comparing these hyperalgesia values of the groups treated with product with those of the group treated with the vehicle only.

In table 5 the results obtained with the compound of example 3 and summarised and in table 6 the ED-50 is presented, showing that this product is more active that other selective inhibitors of COX-2 in the assay of activity against thermal hyperalgesia.

TABLE 5

Analgesic activity against hyperalgesia by thermal stimulus

| Product (Dose = 40 mg/kg, po) | % Activity |
|---|---|
| Example 3 | 100% |
| Nimesulide | 97% |
| Nabumetone | 95% |

TABLE 6

ED-50 of analgesic activity against hyperalgesia by thermal stimulus

| Product | ED-50 (mg/kg, po) |
|---|---|
| Example 3 | 0.2 |
| Nimesulide | 1.0 |
| Nabumetone | 2.1 |

Gastrointestinal Effects (GI): Induction of Ulcers in Rats Submitted to Cold Stress In this assay possible ulcerogenic effects at a gastrointestinal level were determined after oral administration. To do this a modification of the method described by K. D. Rainsford (Agents and actions, 1975, 5, 553–558) was followed. Firstly the rats received the products under study orally at different doses. After two hours had elapsed the rats were placed in a chest freezer at −15° C. for 1 hour. Afterwards they were left for 1 hour at room temperature The animals were then sacrificed and the stomach extracted. The stomach was kept in saline solution for 15 minutes After this time the percentage of surface area with gastric ulcers was determined using a Project C.S.V. vs 1.2 image analyser for each stomach. For each product the maximum dose that did not lead to ulcerogenesis was determined by linear regression analysis of the dose-response.

The results obtained with the compound of example 3 are summarised in table 7. It has been shown not to have ulcerogenic effects, even at very high doses, as was to be expected from a COX-2 selective product. On the other hand, both dichlorophenac and piroxicam, selective COX-1 inhibitors, exhibited ulcerogenic effects at very low doses.

TABLE 7

Induction of ulcers in rats submitted to cold stress.

| Product | Maximum non-Ulcerogenic dose (mg/kg, po) |
|---|---|
| Example 3 | >80 |
| Dichlophenac | 1.2 |
| Piroxicam | 1.7 |

Anti-arthritic Activity in Rat

In this study the anti-arthritic activity in rat of the compound of example 3 has been studied. To do so the method described by B. J. Jaffee et al. (Agents and Actions, 1989, 27, 344–346) was followed. Firstly, the Freund adjuvant was injected (Mycobacterium butiricum suspended in soy-bean oil) through the sub-sole of the back left paw of the rats. After 14 days, when the secondary inflammation had developed in the uninjected paw, which is considered the experimental arthritis, treatment with the product under study or with the vehicle for the control group was started. The compound of example 3 was administered orally at a dose of 10 mg/kg/day for 11 days. The volume of the paw with secondary inflammation in the last days of treatment was measured. The anti-arthritic activity was calculated by comparing the average volume of the paw with secondary inflammation of the group treated with the compound of example 3 and the control group for 5 days.

The results obtained show that the compound of example 3 has a high anti-arthritic activity, as treatment with 10 mg/kg/day, po, led to an inhibition of secondary inflammation, i.e. of an anti-arthritic activity, or 71%.

On the basis of their good pharmacodynamic properties, the derivatives of pyrazolines in accordance with the invention, can be used in satisfactory manner in human and animal therapy, in particular as anti-inflammatory agents for the treatment of inflammation and for the treatment of other disorders associated with inflammation, such as anti-arthritics, analgesics for the treatment of pain and migraine, or as antipyretics in the treatment of fever.

In human therapy, the administration dose of the compounds of the present invention varies as a function of the seriousness of the affliction to treat. Normally the dose will lie between 100 and 400 mg/day. The compounds of the invention will be administered, for example, in the form of capsules, tablets, or injectable solutions or suspensions.

Below, by way of example, two pharmaceutical compositions containing the compounds object of the present invention are shown.

Pharmaceutical Formulations

Example of Formula Per Tablet:

| | |
|---|---|
| Example 3 | 50 mg |
| Corn flour | 16 mg |
| Colloidal silicon dioxide | 1 mg |
| Magnesium stearate | 1 mg |
| Povidone K-90 | 3 mg |
| Pre-gelatinased starch | 4 mg |
| Micro-crystalline cellulose | 25 mg |
| Lactose | 200 mg |

Example of Formula For Capsule:

| | |
|---|---|
| Example 3 | 100 mg |
| Corn flour | 20 mg |
| Colloidal silicon dioxide | 2 mg |
| Magnesium stearate | 4 mg |
| Lactose | 200 mg |

What is claimed is:

1. A derivative of pyrazoline of formula (I)

(I)

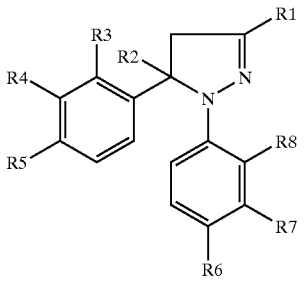

wherein $R_1$ represents hydrogen, a methyl, fluoromethyl, difluormethyl, trifluoromethyl, carboxylic acid, lower carboxylate of 1 to 4 carbon atoms, carboxamide or cyano group;

$R_2$ represents a hydrogen or methyl group;

$R_3$, $R_4$, $R_7$ and $R_8$, are the same or different, represent hydrogen, chlorine, fluorine, methyl, trifluoromethyl or methoxy group;

$R_5$ represents hydrogen, chlorine, fluorine, methyl, trifluoromethyl, methoxy, trifluoromethoxy, methylsulphonyl, aminosulphonyl or acetoaminosulphonyl group;

$R_6$ represents hydrogen, chlorine, fluroine, methyl, or trifluromethyl, methoxy, trifluoromethoxy, methylsulphonyl, aminosulphonyl or acetylaminosulphonyl group, with the provisio that one of $R_5$ or $R_6$ represents hydrogen, chlorine, fluorine, methyl, trifluoromethyl, methoxy, or trifluoromethoxy and the other of $R_5$ or $R_6$ represents a methylsulfonyl, aminosulphonyl, or a acetylaminosulphonyl group;

with the provision that when $R_1$ represents a methyl group then $R_2$ represents a hydrogen atom or a methyl group;

$R_3$ and $R_8$, are the same or different, and represent hydrogen, chlorine, fluorine, methyl or trifluoromethyl group;

$R_4$ represents hydrogen, fluorine, methyl, trifluoromethyl or methoxy group;

$R_5$ represents fluorine, triflouromethyl, trifluoromethoxy, and $R_6$ methylsulfonyl or amino sulphonyl group;

$R_6$ represents hydrogen, chlorine, fluorine, methyl, trifluoromethyl, methoxy, trifluoromethoxy, methylsulphonyl or aminosulphonyl group, with the proviso that one of $R_5$ or $R_6$ represents hydrogen, chlorine, fluorine, methyl, trifluoromethyl, and the other of $R_5$ or $R_6$ represent methylsulphonyl or aminosulphonyl; and $R_7$ represents hydrogen, chlorine, fluorine, methyl, trifluoromethyl or methoxy group; or a physiologically acceptable salt thereof.

2. A compound according to claim 1, selected from the group: consisting of 1-(4-aminosulfonylphenyl)-4,5-dihydro-5-(4-methylphenyl)-3-trifluoromethyl 1H-pyrazole;

1-(4-aminosulphonylphenyl)-4,5-dihydro-5-methyl-5-(4-methylphenyl)-3-trifluoromethyl-1H-pyrazole;

1-(4-aminosulphonylphenyl)-5-(2,4-difluorophenyl-4,5-dihydro-3-trifluoromethyl-1H-pyrazole;

4,5-dihydro-1-(4-methylphenyl)-5-(4-methylsulphonylphenyl)-3-trifluoromethyl-1H-pyrazole;

1-(4-aminosulfonylphenyl)-4,5-dihydro-5-phenyl-3-trifluoromethyl-1H-pyrazole;

4,5-dihydro-5-phenyl- 1-(4-methylsulphonylphenyl)-3-trifluoromethyl-1H-pyrazole;

4,5-dihydro-5-(4-methylphenyl)-1-(4-methylsulphonylphenyl)-3-trifluoromethyl-1H-pyrazole;

1-(4-aminosulphonylphenyl)-4,5-dihydro-5-(4-fluorophenyl)-3-trifluoromethyl -1H-pyrazole;

4,5-dihydro-5-(4-fluorophenyl)-1-(4-methylsulphonylphenyl)-3-trifluoromethyl-1H-pyrazole;

4,5-dihydro-1-(4-fluorophenyl)-5-(4-methylsulphonylphenyl)-3-trifluoromethyl-1H-pyrazole;

1-(4-aminosulphonylphenyl)-5-(3,4-difluorophenyl)-4,5-dihydro-3-trifluoromethyl-1H-pyrazole;

5-(2,4-dichlorophenyl)-4,5-dihydro-1-(4-methylsulphonylphenyl)-3-trifluoromethyl-1H-pyrazole;

1-(4-aminosulfonylphenyl)-5-(2,4-dichlorophenyl)-4,5-dihydro-3-trifluoromethyl-1H-pyrazole;

1-(4-aminosulfonylphenyl)-4,5-dihydro-5-(2-methylphenyl)-3-trifluoromethyl-1H-pyrazole;

1-(4-aminosulfonylphenyl)-4,5-dihydro-5-(3-methylphenyl)-3-trifluoromethyl-1H-pyrazole;

1-(4-aminosulfonylphenyl)-4,5-dihydro-5-(2-fluorophenyl)-3-trifluoromethyl-1H-pyrazole;

4,5-dihydro-5-(2-fluorophenyl)-1-(4-methylsulphonylphenyl)-3-trifluoromethyl-1H-pyrazole;

1-(4-aminosulfonylphenyl)-4,5-dihydro-5-(3-fluorophenyl)-3-trifluoromethyl-1H-pyrazole;

1-(4-aminosulfonylphenyl)-4,5-dihydro-5-(3-fluorophenyl)-3-trifluoromethyl-1H-pyrazole;

4,5-dihydro-5-(3-fluorophenyl)-1-(4-methylsulphonylphenyl)-3-trifluoromethyl-1H-pyrazole;

1-(4-aminosulfonylphenyl)-4,5-dihydro-5-(4-methoxyphenyl)-3-trifluoromethyl-1H-pyrazole;

1-(4-aminosulfonylphenyl)-5-(3-chloro-4-fluorophenyl)-4,5-dihydro-3-trifluoromethyl-1H-pyrazole;

1-(4-aminosulfonylphenyl)-4,5-dihydro-3-trifluoromethyl-5-(4-trifluoromethoxyphenyl)-3-trifluoromethyl-1H-pyrazole;

1-(4-aminosulfonylphenyl)-5-(2,3-difluorophenyl)-4,5-dihydro-3-trifluoromethoxyphenyl-1H-pyrazole;

1-(4-aminosulfonylphenyl)-4,5-dihydro-5-(2,4-dimethylphenyl)-3-trifluoromethyl-1H-pyrazole;

5-(3,4-difluorophenyl)-4,5-dihydro-1-(4-methylsulphonylphenyl)-3-trifluoromethyl-1H-pyrazole;

1-(4-aminosulfonylphenyl)-4,5-dihydro-5-(4-fluorophenyl)-3-methyl-1H-pyrazole;

4,5-dihydro-5-(4-fluorophenyl)-3-methyl-1-(4-methylsulphonylphenyl)-1H-pyrazole;

1-(4-aminosulfonylphenyl)-4,5-dihydro-3-methyl-5-(4-methylphenyl)-1H-pyrazole;

4,5-dihydro-3-methyl-5-(4-methylphenyl)-1-(4-methylsulphonylphenyl)-1H-pyrazole;

1-(4-aminosulphonylphenyl)-4,5-dihydro-3-methyl-5-(4-trifluoromethylphenyl)-1H-pyrazole;

1-(4-aminosulphonylphenyl)-4,5-dihydro-5-(4-methylphenyl)-1H-pyrazole-3-carboxylic acid;

1-(4-aminosulphonylphenyl)-4,5-dihydro-5-phenyl-1H-pyrazole-3-carboxylic acid;

4,5-dihydro-5-(4-methylphenyl)-1-(4-methylsulphonylphenyl)-1H-pyrazole-3-carboxylic acid;

Methyl 1-(4-aminosulphonylphenyl)-4,5-dihydro-5-(4-methylphenyl)-1H-pyrazole-3-carboxylate;

Methyl 1-(4-aminosulphonylphenyl)-4,5-dihydro-5-phenyl-1H-pyrazole-3-carboxylate;

Methyl 4,5-dihydro-5-(4-methylphenyl)-1-(4-methylsulphonylphenyl)-1H-pyrazole-3-carboxylate;

1-(4-aminosulphonylphenyl)-4,5-dihydro-5-phenyl-1H-pyrazole-3-carboxamide;

1-(4-aminosulphonylphenyl)-4,5-dihydro-5-(4-methylphenyl)-1H-pyrazole-3-carboxamide;

4,5-dihydro-5-(4-methylphenyl)-1-(4-methylsulphonylphenyl)-1H-pyrazole-3-carboxamide;

3-cyano-4,5-dihydro-5-(4-methylphenyl)-1-(4-methylsulphonylphenyl)-1H-pyrazole;

1-(4-aminosulphonylphenyl)-4,5-dihydro-5-(3,4-dimethylphenyl)-3-trifluoromethyl-1H-pyrazole;

1-(4-aminosulphonylphenyl)-4,5-dihydro-5-(3-methyl-4-methoxyphenyl-3-trifluoromethyl-1H-pyrazole;

1-(4-aminosulphonylphenyl)-4,5-dihydro-5-(3-fluoro-4-methoxyphenyl)-3-trifluorome-til-1H-pyrazole;

1-(4-aminosulphonylphenyl)-4,5-dihydro-5-(2-fluoro-4-methoxyphenyl)-3-trifluorome-til-1H-pyrazole;

1-(4-aminosulphonylphenyl)-4,5-dihydro-5-(2,4-dimenthoxyphenyl)-3-trifluoromethyl-1H-pyrazole;

1-(4-aminosulphonylphenyl)-4,5-dihydro-5-(4-fluoro-2-methoxyphenyl)-3-trifluoromethyl-1H-pyrazole;

1-(4-aminosulphonylphenyl)-3-difluoromethyl-4,5-dihydro-5-(2,4-dimethylphenyl)-1H-pyrazole;

1-(4-aminosulphonylphenyl)-4,5-dihydro-5-(2,3,4-trifluorophenyl)-3-trifluoromethyl-1H-pyrazole;

1-(4-aminosulphonylphenyl)-5-(2-chloro-4-fluorophenyl)-4,5-dihydro-3-trifluoromethyl-1H-pyrazole;

1-(4-aminosulphonylphenyl)-4,5-dihydro-5-(2-fluoro-4-trifluoromethylphenyl)-3-trifluoromethyl-1H-pyrazole;

1-(4-aminosulphonylphenyl)-5-4,5-dihydro-3-trifluoromethyl-1H-pyrazole;

1-(4-aminosulphonylphenyl)-4,5-dihydro-5-(2-methyl-3-fluorophenyl)-3-trifluoromethyl-1H-pyrazole;

1-(4-aminosulphonylphenyl)-4,5-dihydro-5-(2-methyl-4-methoxyphenyl)-3-trifluoromethyl-1H-pyrazole;

1-(4-aminosulphonylphenyl)-5-(2,4-difluorophenyl)-3-difluoromethyl-4,5-dihydro-1H-pyrazole;

1-(4-aminosulphonylphenyl)-4,5-dihydro-5-(4-fluoro-2-trifluoromethylphenyl)-3-trifluoromethyl-1H-pyrazole;

1-(2,4-difluorophenyl)-4,5-dihydro-5-(4-methylsulphonylphenyl)-3-trifluoromethyl-1H-pyrazole;

1-(4-aminosulphonylphenyl)-5-(2-chlorophenyl)-4,5-dihydro-3-trifluoromethyl-1H-pyrazole;

1-(4-aminosulphonylphenyl)-5-(4-chloro-2-fluorophenyl)-4,5-dihydro-3-trifluoromethyl-1H-pyrazole;

1-(4-aminosulphonylphenyl)-4,5-dihydro-5-(4-fluoro-2-methylphenyl)-3-trifluoromethyl-1H-pyrazole;

1-(4-aminosulphonylphenyl)-4,5-dihydro-5-(2-fluoro-4-methylphenyl)-3-trifluoromethyl-1H-pyrazole;

1-(4-acetylaminosulphonylphenyl)-5-(2,4-difluorophenyl)-4,5-dihydro-3-trifluoromethyl-1H-pyrazole;

1-(4-chlorophenyl)-4,5-dihydro-5-(4-methylsulphonylphenyl)-3-trifluoromethyl-1H-pyrazole;

4,5-dihydro-1-phenyl-5-(4-methylsulphonylphenyl)-3-trifluoromethyl-1H-pyrazole;

4,5-dihydro-1-(2-fluorophenyl)-5-(4-methylsulphonylphenyl)-3-trifluoromethyl-1H-pyrazole;

1-(4-chloro-2-methylphenyl)-4,5-dihydro-5-(4-methylsulphonylphenyl)-3-trifluoromethyl-1H-pyrazole;

4,5-dihydro-1-(3-fluorophenyl)-5-(4-methylsulphonylphenyl)-3-trifluoromethyl-1H-pyrazole;

4,5-dihydro-1-(3-methylphenyl)-5-(4-methylsulphonylphenyl)-3-trifluoromethyl-1H-pyrazole;

4,5-dihydro-1-(2,4-dimethylphenyl)-5-(4-methylsulphonylphenyl)-3-trifluoromethyl-1H-pyrazole;

1-(2-chlorophenyl)-4,5-dihydro-5-(4-methylsulphonylphenyl)-3-trifluoromethyl-1H-pyrazole;

4,5-dihydro-1-(2-methylphenyl)-5-(4-methylsulphonylphenyl)-3-trifluoromethyl-1H-pyrazole;

1-(2,4-dichlorophenyl)-4,5-dihydro-5-(4-methylsulphonylphenyl)-3-trifluoromethyl-1H-pyrazole;

(+)-1-(4-aminosulphonylphenyl)-5-(2,4-difluorophenyl)-4,5-dihydro-3-trifluoromethyl-1H-pyrazole;

(−)-1-(4-aminosulphonylphenyl)-5-(2,4-difluorophenyl)-4,5-dihydro-3-trifluoromethyl-2H-pyrazole;

(+)-4,5-dihydro-1-(4-fluorophenyl)-5-(4-methylsulphonylphenyl)-3-trifluoromethyl-1H-pyrazole; and (−)-4,5-dihydro-1-(4-fluorophenyl)-5-(4-methylsulphonylphenyl)-3-trifluoromethyl-1H-pyrazole;

*4,5-dihydro-5-(4-methyl-sulphonylphenyl)-3-trifluoromethyl)-1-(2-trifluoromethylphenyl)-1H-pyrazole;* or a physiologically acceptable salts thereof.

3. A procedure for preparing a derivative of pyrazoline of formula (I), according to claim 1, by reacting a compound of formula (II)

(II)

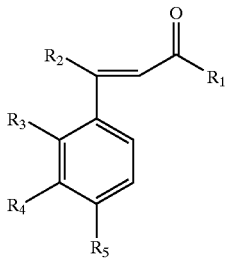

wherein $R_1$ represents hydrogen, methyl, fluoromethyl, difluoromethyl, trifluoromethyl and carboxylic acid groups, and $R_2$, $R_3$, $R_4$ and $R_5$ have the same meaning as claimed in claim 1, with a phenylhydrazine of formula (III) in base or salt form (III)

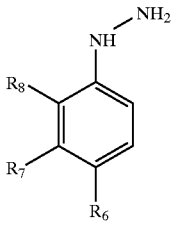

wherein $R_6$, $R_7$ and $R_8$ have the same meaning as claimed in claim 1.

4. A procedure for the preparation of a derivative of pyrazoline of general formula (I), according to claim 1, wherein $R_1$, represents an alkyl carboxylate with less than 1 to 4 carbon atoms and $R_2$, $R_3$, $R_4$, $R_5$, $R_6$, $R_7$ and $R_8$ have the same meaning as that claimed in claim 1, which comprises reacting a compound of formula (I) in which $R_1$ represents a carboxylic acid group (COOH) and $R_2$, $R_3$, $R_4$, $R_5$, $R_6$, $R_7$ and $R_8$ have the same meaning as that claimed in claim 1, with a suitable reagent to form the acid chloride, and then carrying out an esterification reaction with an aliphatic alcohol of 1 to 4 carbon atoms in the presence of an organic base, or by direct reaction of carboxylic acid with the corresponding saturated anhydrous alcohol with gaseous hydrogen chloride.

5. A procedure for the preparation of a derivative of pyrazoline of formula (I), according to claim 1, wherein $R_1$ represents a carboxylic acid group and $R_2$, $R_3$, $R_4$, $R_5$, $R_6$, $R_7$ and $R_8$ have the same meaning as claimed in claim 1, which comprises reacting a compound of formula (I) wherein R1 represents a carboxylic acid group (COOH) and $R_2$, $R_3$, $R_4$, $R_5$, $R_6$, $R_7$ and $R_8$ have the same meaning as claimed in claim 1, with a suitable reagent for forming the corresponding acid chloride, and then reacting with ammonia.

6. A procedure for the preparation of a derivative of pyrazoline of general formula (I), according to claim 1, wherein $R_1$ represents a cyano group and $R_2$, $R_3$, $R_4$, $R_5$, $R_6$, $R_7$ and $R_8$ have the same meaning as claimed in claim 1, which comprises reacting a compound of formula (I) wherein $R_1$ represents a carboxamide group and $R_2$, $R_3$, $R_4$, $R_5$, $R_6$, $R_7$ and $R_8$ have the same meaning as that indicated in claim 1, with either thionyl dimethylformamide-chloride or methanosulphonyl chloride.

7. A procedure for the preparation of a derivative of pyrazoline of formula (I), according to claim 1, wherein $R_1$, $R_2$, $R_3$, $R_4$, $R_5$, $R_7$ and $R_8$ have the same meaning as that claimed in claim 1 and $R_6$ represents an acetylaminosulphonyl group, or $R_1$, $R_2$, $R_3$, $R_4$, $R_6$, $R_7$ and $R_8$ have the same meaning as that claimed in claim 1 and $R_5$ represents an acetylaminosulphonyl group, which comprises reacting a compound of formula (I) wherein $R_1$, $R_2$, $R_3$, $R_4$, $R_5$, $R_7$ and $R_8$ have the meaning claimed in claim 1 and $R_6$ represents a aminosulphonyl group, or $R_1$, $R_2$, $R_3$, $R_4$, $R_6$, $R_7$ and $R_8$ have the meaning claimed in claim 1 and $R_5$ represents a aminosulphonyl group, with, either acetyl chloride or acetic anhydride.

8. Procedure for the preparation of a derivative of pyrazoline of formula (I), according to claim 1, enantiomerically pure, which comprises effecting the resolution of a racemic mixture of the compound of formula (I) by chromatography with chiral stationary phase or formation of a salt with an enantiomerically pure acid.

9. A procedure for the preparation of a physiologically acceptable salt of a derivative of pyrazoline of formula (I), according to claim 1, which comprises reacting a compound of formula (I) with an inorganic acid or with an organic acid in the presence of a suitable solvent.

10. A pharmaceutical composition, containing at least, a derivative of pyrazoline of formula (I), or a physiologically acceptable salt thereof, according to claim 1, and pharmaceutically acceptable excipients.

11. A method of treatment of inflammation or of the treatment of other disorders associated with inflammation comprising administering a derivative of pyrazoline of formula (I), or a pharmaceutically acceptable salt thereof, according to claim 1, to a patient in need thereof.

12. The method of treatment according to claim 11, wherein the disorder associated with inflammation is arthritis.

13. The method of treatment according to claim 11, wherein the disorder associated with inflammation is pain.

14. The method of treatment according to claim 11, wherein the disorder associated with inflammation is fever.

15. The procedure according to claim 4 wherein the suitable reagent to for the acid chloride is thionyl chloride or oxalyl chloride.

16. The procedure according to claim 4 wherein the organic base is triethylamine or pyridine.

17. The procedure according to claim 5 wherein the suitable reagent to form the corresponding acid chloride is thionyl chloride or oxalyl chloride.

18. A method for treating a migraine comprising administering a derivative of pyrazoline of formula (I) according to claim 1 or a pharmaceutically acceptable salt thereof to a patient in need thereof.

19. A method for treating menstrual disorders comprising administering a derivative of pyrazoline of formula (I) according to claim 1 or a pharmaceutically acceptable salt thereof to a patient in need thereof.

20. A method for treating asthma or bronchitis comprising administering a derivative of pyrazoline of formula (I) according to claim 1 or a pharmaceutically acceptable salt thereof to a patient in need thereof.

21. A method for treating skin disorders selected from psoriasis, eczema, burns and dermatitis comprising administering a derivative of pyrazoline of formula (I) according to claim 1 or a pharmaceutically acceptable salt thereof to a patient in need thereof.

22. A method for treating tendinitis or bursitis comprising administering a derivative of pyrazoline of formula (I) according to claim 1 or a pharmaceutically acceptable salt thereof to a patient in need thereof.

23. A method for treating gastrointestinal afflications selected from inflamed intestine, Crohn's disease, gastritis, irritated colon syndrome and ulcerous colitis comprising administering to claim 1 or a pharmaceutically acceptable salt to a patient in need thereof.

* * * * *